US007423147B2

(12) United States Patent  
Carruthers et al.

(10) Patent No.: US 7,423,147 B2  
(45) Date of Patent: Sep. 9, 2008

(54) PYRIDINE COMPOUNDS AS HISTAMINE H3 MODULATORS

(75) Inventors: Nicholas I. Carruthers, Poway, CA (US); Chandravadan R. Shah, San Diego, CA (US); Devin M. Swanson, La Jolla, CA (US)

(73) Assignee: Janssen Pharmaceutical, N.V., Beerse (BE)

( * ) Notice: Subject to any disclaimer, the term of this patent is extended or adjusted under 35 U.S.C. 154(b) by 374 days.

(21) Appl. No.: 11/095,398

(22) Filed: Mar. 31, 2005

(65) Prior Publication Data

US 2005/0222151 A1 Oct. 6, 2005

Related U.S. Application Data

(60) Provisional application No. 60/557,959, filed on Mar. 31, 2004.

(51) Int. Cl.  
*C07D 241/04* (2006.01)  
*C07D 265/30* (2006.01)  
*C07D 295/00* (2006.01)

(52) U.S. Cl. ..................... 544/106; 544/358
(58) Field of Classification Search .................. None  
See application file for complete search history.

(56) References Cited

U.S. PATENT DOCUMENTS

| 3,538,106 | A | 11/1970 | Hoffmann et al. |
| 4,792,547 | A | 12/1988 | Itoh et al. |
| 5,780,393 | A | 7/1998 | Newton |
| 6,201,007 | B1 * | 3/2001 | Ito et al. ..................... 514/422 |
| 6,399,607 | B1 | 6/2002 | Welch et al. |
| 6,645,990 | B2 * | 11/2003 | Askew et al. ............... 514/342 |
| 2003/0125339 | A1 | 7/2003 | Chen et al. |
| 2004/0224968 | A1 | 11/2004 | Seidelmann et al. |

FOREIGN PATENT DOCUMENTS

| CA | 1051888 A1 | 4/1979 |
| DE | 817911 C | 10/1951 |
| DE | 1902694 A1 | 9/1969 |
| DE | 2514334 A1 | 10/1987 |
| EP | 0089153 A2 | 9/1983 |
| EP | 0134096 A2 | 3/1985 |
| EP | 0143630 A2 | 6/1985 |
| EP | 1 388 535 A1 | 2/2004 |
| EP | 1396487 A1 | 3/2004 |
| JP | 44 020347 B | 9/1969 |
| JP | 46 037595 B | 11/1971 |
| JP | 06306051 * | 11/1994 |
| WO | WO 84/04304 A1 | 11/1984 |
| WO | WO 00/50391 A1 | 8/2000 |
| WO | WO 00/76984 A2 | 12/2000 |
| WO | WO 01/85715 A2 | 11/2001 |
| WO | WO 03/37869 A1 | 5/2003 |
| WO | WO 03/37891 A1 | 5/2003 |
| WO | WO 03/66604 A2 | 8/2003 |
| WO | WO 03/78398 A1 | 9/2003 |
| WO | WO 03/82205 A2 | 10/2003 |
| WO | WO 03/92686 A1 | 11/2003 |
| WO | WO 2004/18428 A1 | 3/2004 |
| WO | WO 2004/054973 A2 | 7/2004 |
| WO | WO 2005/007644 A1 | 1/2005 |
| WO | WO 2005/009976 A1 | 2/2005 |
| WO | WO 2005/23247 A1 | 3/2005 |

OTHER PUBLICATIONS

LaVoie and patani. Chemical Reviews, 1996, 96, 3147-3176.*  
Vippagunta et al. Advanced Drug Delivery Reviews, 2001, 48, 3-26.*  
Akhundov et al., "Synthesis and Psychotropic Activity of Amides of 2-aminonicotinic Acid", *Khimiko-Farmatsevticheskki Zhurnal*, vol. 20, No. 1 (1986) pp. 48-50, Rumoscow, Database Beilstein 1993, Database accession No. 5702704 (CNR) BRN: 5598995, 5632883, 5764929, 5774681, (XP002344011).  
Buchi et al., "Syntheses of Some 2-Dialkylaminoalkoxy-6-alkylaminopyridines and 2-dialkylaminoalkylamino-6-alkoxypyridines", *Helvetica Chimica Acta.*, vol. 48, No. 5 (1965) pp. 1216-1219, Chverlag Helvetica Chimica Acta. Basel, (XP009050917).  
Highfield et al., "Preparative, Physico-Chemical and Cytotoxicity Studies of Prodrugs Activated in Hyposiz to Give Metal-Binding Analogues of Bleomycin", *Journal of the Chemical Society*, Perkin Transactions 1, vol. 16 (1999) pp. 2343-2352, GB Chemical Society, Letchworth, (XP002337176).  
Pavia et al., "N,N-Disubstituted 6-Alkoxy-2-Pyridinamines as Anticonvulsant Agents", *Journal of the American Chemical Society*, vol. 30, No. 7 (1987) pp. 1210-1214, US American Chemical Society, Washington DC, (XP002337175).  
Stark, "Recent Advances in Histamine $H_3/H_4$ Receptor Ligands", *Expert Opinion on Therapeutic Patents*, vol. 13, No. 6 (2003) pp. 851-865, Ashley Publications, GB, ISSN: 1354-3776, (XP002298271).  
Thunus et al., "Quelques Derives de la (Methyl-4, Peperazinyl-1)-2 Pyridine Substituee en 3", *European Journal of Medicinal Chemistry*, vol. 9, No. 1 (1974) pp. 55-58, Freditions Scientifique Elsevier, Paris, (XP009050898), No.  
"Phenylalkynes to Treat Histamine-Mediated Conditions", *Expert Opinion on Therapeutic Patents*, vol. 13, No. 11 (2003) pp. 1759-1762, Gbashley Publications, (XP002337280).  
Arrang, J.-M. et al. Auto-inhibition of Brain Histamine Release Mediated by a Novel Class ($H_3$) of Histamine Receptor. *Nature* 1983, 302, 832-837.  
Ash, A.S.F.; Schild, H.O. Receptors Mediating Some Actions of Histamine. *Br. J. Pharmac. Chemother.* 1966, 27, 427-439.  
Barnes, J.C. et al. The Selective Histamine H3 Receptor Antagonist Thioperamide Improves Cognition and Enhances Hippocampal Acetylcholine Release In Vivo. *Soc. Neurosci. Abstr.* 1993, 19, 1813.  
Black, J.W. et al. Definition and Antagonism of Histamine $H_2$-Receptors. *Nature* 1972, 236, 385-390.

(Continued)

*Primary Examiner*—James O. Wilson  
*Assistant Examiner*—Noble Jarrell

(57) ABSTRACT

Certain non-imidazole heterocyclic compounds are Histamine $H_3$ modulators in the treatment of Histamine $H_3$ receptor mediated diseases.

6 Claims, No Drawings

OTHER PUBLICATIONS

Ganellin, C.R. et al. Synthesis of Potent Non-Imidazole Histamine $H_3$-Receptor Antagonists. *Arch. Pharm. Pharm. Med. Chem. (Weinheim, Ger.)* 1998, 331, 395-404.

Ichinose, M.; Barnes, P.J. Histamine $H_3$-Receptors Modulate Nonadrenergic Noncholinergic Neural Bronchoconstriction in Guinea-Pig In Vivo. *Eur. J. Pharmacol.* 1989, 174(1), 49-55.

Imamura, M. et al. Unmásking of Activated Histamine $H_3$-Receptors in Myocardial Ischemia: Their Role as Regulators of Exocytotic Norepinephrine Release. *J. Pharmacol. Exp. Ther.* 1994, 271(3), 1259-1266.

Krause, M. et al. Medicinal Chemistry of Histamine $H_3$ Receptor Agonists. In *The Histamine $H_3$ Receptor—A Target for New Drugs*. Leurs, R.; Timmerman, H., Eds.; Elsevier: 1998; pp. 175-196.

Letavic, M.A. et al. Recent Medicinal Chemistry of the Histamine $H_3$ Receptor. Prog. in Med. Chem., in press.

Leurs, R. et al. The Medicinal Chemistry and Therapeutic Potentials of Ligands of the Histamine $H_3$ Receptor. *Prog. Drug Res.* 1995, 45, 107-165.

Lin, J.-S. et al. Involvement of Histaminergic Neurons in Arousal Mechanisms Demonstrated with $H_3$-Receptor Ligands in the Cat. *Brain Res.* 1990, 523, 325-330.

Linney, I.D. et al. Design, Synthesis, and Structure-Activity Relationships of Novel Non-Imidazole Histamine $H_3$ Receptor Antagonists. *J. Med. Chem.* 2000, 43(12), 2362-2370.

Lovenberg, T.W. et al. Cloning and Functional Expression of the Human Histamine $H_3$ Receptor. *Mol. Pharmacol.* 1999, 55(6), 1101-1107.

MacDonald, S.J.F. et al. Discovery of Further Pyrrolidine trans-Lactams as Inhibitors of Human Neutrophil Elastase (HNE) with Potential as Development Candidates and the Crystal Structure of HNE Complexed with an Inhibitor (GW475151). *J.Med.Chem.* 2002, 45(18), 3878-3890.

Machidori, H. et al. Zucker Obese Rats: Defect in Brain Histamine Control of Feeding. *Brain Res.* 1992, 590, 180-186.

Mase, T. et al. Synthesis of Muscarinic Receptor Antagonist via a Diastereoselective Michael Reaction, Selective Deoxyfluorination and Metal-Halogen Exchange Reaction. *J. Org. Chem.* 2001, 66, 6775-6786.

McLeod, R.L. et al. Antimigraine and Sedative Activity of SCH 50971: A Novel Orally-Active Histamine $H_3$ Receptor Agonist. *Soc. Neurosci. Abstr.* 1996, 22, 2010.

Monti, J.M. et al. Effects of Selective Activation or Blockade of the Histamine $H_3$ Receptor on Sleep and Wakefulness. *Eur. J. Pharmacol.* 1991, 205(3), 283-287.

Morisset, S. et al. High Constitutive Activity of Native $H_3$ Receptors Regulates Histamine Neurons in Brain. *Nature* 2000, 408, 860-864.

Panula, P. et al. Significant Changes in the Human Brain Histaminergic System in Alzheimer's Disease. *Soc. Neurosci. Abstr.* 1995, 21, 1977.

Phillips, J.G. and S.M. Ali. Medicinal Chemistry of Histamine $H_3$ Receptor Antagonists. In *The Histamine $H_3$ Receptor—A Target for New Drugs*. Leurs, R.; Timmerman, H., Eds.; Elsevier: 1998; pp. 197-222.

Reiner, J.E. et al. Non-Covalent Thrombin Inhibitors Featuring $P_3$-Heterocycles with $P_1$-Monocyclic Arginine Surrogates. *Bioorg. Med. Chem. Lett.* 2002, 12, 1203-1208.

Schlicker, E.; Marr, I. The Moderate Affinity of Clozapine at $H_3$ Receptors Is Not Shared by Its Two Major Metabolites and by Structurally Related and Unrelated Atypical Neuroleptics. *Naunyn-Schmiedeberg's Arch. Pharmacol.* 1996, 353, 290-294.

Stark, H. et al. Developments of Histamine $H_3$-Receptor Antagonists. *Drugs Future* 1996, 21(5), 507-520.

Tozer, M.J.; Kalindjian, S.B. Histamine $H_3$ Receptor Antagonists. *Exp. Opin. Ther. Patents* 2000, 10(7), 1045-1055.

Turner, S.C. et al. A New Class of Histamine $H_3$-Receptor Antagonists: Synthesis and Structure-Activity Relationships of 7,8,9,10-Tetrahydro-6H-cyclohepta[b]quinolones. *Bioorg. Med. Chem. Lett.* 2003, 13(13), 2131-2136.

Walczynski, K. et al. Non-Imidazole Histamine $H_3$ Ligans. Part I. Synthesis of 2-(1-Piperazinyl)- and 2-(Hexahydro-1H-1,4-diazepin-1-yl)benzothiazole Derivatives as H3-Antagonists with H1 Blocking Activities. *Farmaco* 1999, 54, 684-694.

Walczynski, K. et al. Non-Imidazole Histamine H3 Ligands, Part 2: New 2-Substituted Benzothiazoles as Histamine H3 Antagonists. *Arch. Pharm. Pharm. Med. Chem.* (Weinheim, Ger.) 1999, 332, 389-398.

Yokoyama, H. et al. Effect of Thioperamide, a Histamine $H_3$ Receptor Antagonist, on Electrically Induced Convulsions in Mice. *Eur. J. Pharmacol.* 1993, 234, 129-133.

Partial International Search Report dated Sep. 21, 2005, for corresponding international application PCT/US2005/010570.

Foks et al, "Pyrazine derivatives. III. Synthesis and tuberculostatic activity of 6-(N-methyllamino)-pyrazine-2-carboxylic acid derivates", Polish Journal of Pharmacology and Pharmary, vol. 26, No. 5 (1974) pp. 537-543 (XP002355523)—Chemical Abstracts, Database accession No. 82:43345 (DN) RN 54409-12-0.

Foks et al, "Aminomethylation of pyridine- and pyrazinecarbothioamides. V. 6-Chloro- and 6-aminopyrazine-2-carbothioamides in the Mannich reaction", ACTA Poloniae Pharmaceutica, vol. 33, No. 1, (1976) pp. 55-65 (XP002355524)—Chemical Abstracts, Database accession No. 86:72575 (DN).

International Search Report dated Dec. 22, 2005, for corresponding international application PCT/US2005/010570.

* cited by examiner

PYRIDINE COMPOUNDS AS HISTAMINE H3 MODULATORS

This application claims priority to provisional application, which is U.S. Ser. No. 60/557,959 filed Mar. 31, 2004. The complete disclosures of the aforementioned related U.S. patent applications are hereby incorporated herein by reference for all purposes.

FIELD OF THE INVENTION

The present invention relates to a series of 5- and 6-membered nitrogen-containing heterocycles, their synthesis and their use, for example, for the treatment of disorders and conditions mediated by the histamine $H_3$ receptor.

BACKGROUND OF THE INVENTION

Histamine {2-(imidazol-4-yl)ethylamine} is a transmitter substance. Histamine exerts a physiological effect via multiple distinct G-protein coupled receptors. It plays a role in immediate hypersensitivity reactions and is released from mast cells following antigen IgE antibody interaction. The actions of released histamine on the vasculature and smooth muscle system account for the symptoms of the allergic response. These actions occur at the $H_1$ receptor (Ash, A. S. F. and Schild, H. O., Br. J. Pharmac. Chemother. 1966, 27:427-439) and are blocked by the classical antihistamines (e.g. diphenhydramine). Histamine is also an important regulator of gastric acid secretion through its action on parietal cells. These effects of histamine are mediated via the $H_2$ receptor (Black, J. W. et al., Nature 1972, 236:385-390) and are blocked by $H_2$ receptor antagonists (e.g. cimetidine). The third histamine receptor —$H_3$— was first described as a presynaptic autoreceptor in the central nervous system (CNS) (Arrang, J.-M. et al., Nature 1983, 302:832-837) controlling the synthesis and release of histamine. Recent evidence has emerged showing that $H_3$ receptors are also located presynaptically as heteroreceptors on serotonergic, noradrenergic, dopaminergic, cholinergic, and GABAergic (gamma-aminobutyric acid containing) neurons. These $H_3$ receptors have also recently been identified in peripheral tissues such as vascular smooth muscle. Consequently, there are many potential therapeutic applications for histamine $H_3$ agonists, antagonists, and inverse agonists. (See: "The Histamine $H_3$ Receptor-A Target for New Drugs", Leurs, R., and Timmerman, H., (Eds.), Elsevier, 1998; Morisset, S. et al., Nature 2000, 408:860-864.) A fourth histamine receptor —$H_4$— was recently described by Oda, T. et al. (J. Biol. Chem. 2000, 275(47):36781-36786).

The potential use of histamine $H_3$ agonists in sleep/wake and arousal/vigilance disorders is suggested based on animal studies (Lin, J.-S. et al., Brain Res. 1990, 523:325-330; Monti, J. M. et al., Eur. J. Pharmacol. 1991, 205:283-287). Their use in the treatment of migraine has also been suggested (McLeod, R. L. et al., Soc. Neurosci. Abstr. 1996, 22:2010) based on their ability to inhibit neurogenic inflammation. Other applications could include a protective role in myocardial ischemia and hypertension where blockade of norepinephrine release is beneficial (Imamura, M. et al., J. Pharmacol. Exp. Ther. 1994, 271(3):1259-1266). It has been suggested that histamine $H_3$ agonists may be beneficial in asthma due to their ability to reduce non-adrenergic non-cholinergic (NANC) neurotransmission in airways and to reduce microvascular leakage (Ichinose, M. and Barnes, P. J., Eur. J. Pharmacol. 1989, 174:49-55).

Several indications for histamine $H_3$ antagonists and inverse agonists have similarly been proposed based on animal pharmacology experiments with known histamine $H_3$ antagonists (e.g. thioperamide). These include dementia, Alzheimer's disease (Panula, P. et al., Soc. Neurosci. Abstr. 1995, 21:1977), epilepsy (Yokoyama, H. et al., Eur. J. Pharmacol. 1993, 234:129-133), narcolepsy, with or without associated cataplexy, cataplexy, disorders of sleep/wake homeostasis, idiopathic somnolence, excessive daytime sleepiness (EDS), circadian rhythm disorders, sleep/fatigue disorders, fatigue, drowsiness associated with sleep apnea, sleep impairment due to perimenopausal hormonal shifts, jet lag, Parkinson's-related fatigue, multiple sclerosis (MS)-related fatigue, depression-related fatigue, chemotherapy-induced fatigue, eating disorders (Machidori, H. et al., Brain Res. 1992, 590: 180-186), motion sickness, vertigo, attention deficit hyperactivity disorders (ADHD), learning and memory (Barnes, J. C. et al., Soc. Neurosci. Abstr. 1993, 19:1813), and schizophrenia (Schlicker, E. and Marr, I., Naunyn-Schmiedeberg's Arch. Pharmacol. 1996, 353:290-294). (Also see: Stark, H. et al., Drugs Future 1996, 21(5):507-520; and Leurs, R. et al., Prog. Drug Res. 1995, 45:107-165 and references cited therein.) Histamine $H_3$ antagonists, alone or in combination with a histamine $H_1$ antagonist, are reported to be useful for the treatment of upper airway allergic response (U.S. Pat. Nos. 5,217,986; 5,352,707 and 5,869,479). Recently, a histamine $H_3$ antagonist (GT-2331) was identified and is being developed by Gliatech Inc. (Gliatech Inc. Press Release Nov. 5, 1998; Bioworld Today, Mar. 2,1999) for the treatment of CNS disorders.

As noted, the literature related to histamine $H_3$ ligands has been comprehensively reviewed ("The Histamine $H_3$ Receptor—A Target for New Drugs", Leurs, R. and Timmerman, H., (Eds.), Elsevier, 1998). Within this reference the medicinal chemistry of histamine $H_3$ agonists and antagonists was reviewed (see Krause, M. et al., and Phillips, J. G. and Ali, S. M., respectively). The importance of an imidazole moiety containing only a single substitution in the 4-position was noted, together with the deleterious effects of additional substitution on activity. Particularly, methylation of the imidazole ring at any of the remaining unsubstituted positions was reported to strongly decrease activity. Additional publications support the hypothesis that an imidazole function is essential for high affinity histamine $H_3$ receptor ligands (see Ali, S. M. et al., J. Med. Chem. 1999, 42:903-909, and Stark, H. et al., and references cited therein). However, many imidazole-containing compounds are substrates for histamine methyl transferase, the major histamine metabolizing enzyme in humans, which leads to shortened half-lives and lower bioavailability (see Rouleau, A. et al., J. Pharmacol. Exp. Ther. 1997, 281 (3):1085-1094). In addition, imidazole-containing drugs, via their interaction with the cytochrome $P_{450}$ monooxygenase system, can participate in unfavorable biotransformations due to enzyme induction or enzyme inhibition (see: Kapetanovic, I. M. and Kupferberg, H. J., Drug Metab. Dispos. 1984, 12(5):560-564; Sheets, J. J. and Mason, J. I., Drug Metab. Dispos. 1984, 12(5):603-606; Back, D. J. and Tjia, J. F., Br. J. Pharmacol. 1985, 85:121-126; Lavrijsen, K. et al., Biochem. Pharmacol. 1986, 35(11):1867-1878; Albengres, E. et al., Drug Safety 1998, 18(2):83-97). The poor blood brain barrier penetration of earlier histamine $H_3$ receptor ligands may also be associated with the imidazole fragment (Ganellin, C. R. et al., Arch. Pharm. Pharm. Med. Chem. (Weinheim, Ger.) 1998, 331:395-404).

More recently, several publications have described histamine $H_3$ ligands that do not contain an imidazole moiety, for example: Ganellin, C. R. et al.; Walczynski, K. et al., Arch.

Pharm. Pharm. Med. Chem. (Weinheim, Ger.) 1999, 332: 389-398; Walczynski, K. et al., Farmaco 1999, 54:684-694; Linney, I. D. et al., J. Med. Chem. 2000, 43:2362-2370; Tozer, M. J. and Kalindjian, S. B., Exp. Opin. Ther. Patents 2000, 10:1045-1055; U.S. Pat. No. 5,352,707; PCT Application WO 99/42458, Aug. 26, 1999; PCT Application WO 02/076925; and European Patent Application 0978512, Feb. 9, 2000.

In addition, a more recent review of this topic was presented (Tozer, M. T. and Kalindjian, S. B. Exp. Opin. Ther. Patents 2000,10:1045). Additional publications and patents, concerning both histamine $H_3$ agonists and antagonists, have appeared since the publication of the Leurs monograph. Most noteworthy is the development of non-imidazole histamine $H_3$ antagonists (Apodaca et al WO 02/12214; Apodaca et al WO 02/12190; Bogenstaetter et al 02/12224; Carruthers et al WO 01/74810; Chai et al WO 01/74814; Breitenbucher et al WO 01/74815; Breitenbucher et al WO 01/74813; Breitenbucher et al WO 01/74773; Bennani et al WO 02/06223; Bennani et al WO 01/66534; Schwartz et al EP 0978512 A1; Schwartz et al WO 00/06254; Linney et al J. Med. Chem. 2000, 43, 2362; and Ganellin et al Arch. Pharm. Pharm. Med. Chem. 1998, 331, 395).

The compounds of the present invention do not contain the imidazole moiety, and its inherent liabilities, and yet maintain potency at the human $H_3$ receptor as determined by receptor binding to the human histamine $H_3$ receptor (see Lovenberg, T. W. et al., Mol. Pharmacol. 1999, 55:1101-1107). Screening using the human receptor is particularly important for the identification of new therapies for the treatment of human disease. Conventional binding assays, for example, are determined using rat synaptosomes (Garbarg, M. et al., J. Pharmacol. Exp. Ther. 1992, 263(1):304-310), rat cortical membranes (West, R. E. et al., Mol. Pharmacol. 1990, 38:610-613), and guinea pig brain (Korte, A. et al., Biochem. Biophys. Res. Commun. 1990, 168(3):979-986). Only limited studies have been performed previously using human tissue but these allude to significant differences in the pharmacology of rodent and primate receptors (West, R. E. et al., Eur. J. Pharmacol. 1999, 377:233-239).

Described herein is a series of 5- and 6-membered aromatic nitrogen-containing heterocyclic compounds with the ability to modulate the activity of the histamine receptor, specifically the $H_3$ receptor, without the inherent problems associated with the presence of an imidazole moiety.

SUMMARY OF THE INVENTION

The invention features a heterocyclic compound of formula (I):

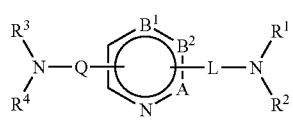

(I)

wherein
in the A- and B-containing ring,
I) A, $B^1$ and $B^2$ are CH;
II) A is CH, one of $B^1$ and $B^2$ is N, and the other of $B^1$ and $B^2$ is CH; or
III) A is absent, $B^1$ is CH, and $B^2$ is O;

L is —$C_{1-4}$alkylene- or a covalent bond;
Q is —$(CH_2)_mO$—, —$(CH_2)_nC\equiv C$— (where the —O— and —C≡C— portions are directly attached to the ring), carbonyl, or thiocarbonyl;
m is 2, 3, or 4;
n is 1, 2, 3, or 4;
$R^1$, optionally mono- or di-substituted with $R^p$, is independently selected from the group consisting of —H, —$C_{1-7}$alkyl, —$C_{2-7}$alkenyl, —$C_{2-7}$alkynyl, —$C_{3-7}$cycloalkyl, phenyl, benzyl, pyridinyl, pyrimidinyl, furanyl, thienyl, pyrrolyl, and a 5-, 6-, or 7-membered monocyclic non-aromatic heterocyclic ring having 1 or 2 heteroatom members selected from O, S, —N=, >NH, and >$NC_{1-4}$alkyl, having 0, 1, or 2 double bonds;
$R^2$, optionally mono- or di-substituted with $R^p$, is independently selected from the group consisting of —$C_{1-7}$alkyl, —$C_{2-7}$alklenyl, —$C_{2-7}$alkynyl, —$C_{3-7}$cycloalkyl, phenyl, benzyl, pyridinyl, pyrimidinyl, furanyl, thienyl, pyrrolyl, and a 5-, 6-, or 7-membered monocyclic non-aromatic heterocyclic ring having 1 or 2 heteroatom members selected from O, S, —N=, >NH, and >$NC_{1-4}$alkyl, having 0, 1, or 2 double bonds;
or, alternatively,
$R^1$ and $R^2$ may be taken together with the nitrogen of attachment to form a ring, said ring selected from the group consisting of:
i) a 4-7 membered non-aromatic heterocyclic ring, said heterocyclic ring having 0 or 1 additional heteroatom members separated from the nitrogen of attachment by at least one carbon member and selected from O, S, —N=, >NH, and >$NC_{1-4}$alkyl, having 0, 1, or 2 double bonds, having 0, 1, or 2 carbon members which is a carbonyl, having 0, 1, or 2 substituents $R^q$; and
ii) a benzo or pyrido fused 4-7 membered non-aromatic heterocyclic ring, said heterocyclic ring having 0 or 1 additional heteroatom members separated from the nitrogen of attachment by at least one carbon member and selected from O, S, —N=, >NH, and >$NC_{1-4}$alkyl, having 0 or 1 additional double bonds, having 0, 1, or 2 carbon members which is a carbonyl, and having 0, 1, or 2 substituents $R^q$;
$R^p$ is independently selected from the group consisting of —$C_{1-6}$alkyl, —$C_{2-6}$alkenyl, —$C_{3-6}$cycloalkyl, phenyl, pyridyl, furanyl, thienyl, benzyl, pyrimidinyl, pyrrolyl, halo, —OH, —$OC_{1-6}$alkyl, —$OC_{3-6}$cycloalkyl, —Ophenyl, —Obenzyl, —SH, —$SC_{1-6}$alkyl, —$SC_{3-6}$cycloalkyl, —Sphenyl, —Sbenzyl, —CN, —$NO_2$, —$N(R^y)R^z$ (wherein $R^y$ and $R^z$ are independently selected from H and $C_{1-4}$alkyl; or $R^y$ and $R^z$ may be taken together with the nitrogen of attachment to form a 5-, 6-, or 7-membered monocyclic heterocyclic ring having 1 or 2 additional heteroatom members selected from O, S, —N=, >NH, and >$NC_{1-4}$alkyl, said ring optionally substituted with —$C_{1-4}$alkyl, —OH, —$OC_{1-4}$alkyl, halo, or —$COOC_{1-4}$alkyl), —(C=O)N($R^y$)$R^z$, —(C=O)$C_{1-4}$alkyl, —$SCF_3$, —$OCF_3$, —$CF_3$, and —$COOC_{1-4}$alkyl, and —COOH;
$R^q$ is independently selected from the group consisting of —$C_{1-6}$alkyl, halo, —OH, —$OC_{1-6}$alkyl, —CN, —$NO_2$, —$CF_3$, and —$COOC_{1-4}$alkyl,
$R^3$, optionally mono- or di-substituted with $R^s$, is independently selected from the group consisting of —H, —$C_{1-7}$alkyl, —$C_{2-7}$alkenyl, —$C_{2-7}$alkynyl, —$C_{3-7}$cycloalkyl, phenyl, benzyl, pyridinyl, pyrimidinyl, furanyl, thienyl, pyrrolyl, and a 5-, 6-, or 7-membered monocyclic non-aromatic heterocyclic ring having 1 or 2 heteroatom members selected from O, S, —N=, >NH, and >$NC_{1-4}$alkyl, having 0, 1, or 2 double bonds; and $R^4$, optionally mono- or di-substituted with $R^s$, is independently selected from the group consisting of —$C_{1-7}$alkyl, —$C_{2-7}$alkenyl, —$C_{2-7}$alkynyl, —$C_{3-7}$cycloalkyl, phenyl, benzyl, pyridinyl, pyrimidinyl, furanyl, thienyl, pyrrolyl, and a 5-, 6-, or 7-membered monocyclic non-aromatic heterocyclic ring having 1 or 2 heteroatom members selected from O, S, —N=, >NH, and >N$C_{1-4}$alkyl, having 0, 1, or 2 double bonds;

$R^s$ is independently selected from the group consisting of —$C_{1-6}$alkyl, —$C_{2-6}$alkenyl, —$C_{3-6}$cycloalkyl, phenyl, pyridyl, furanyl, thienyl, benzyl, pyrimidinyl, pyrrolyl, halo, —OH, —O$C_{1-6}$alkyl, —O$C_{3-6}$cycloalkyl, —Ophenyl, —Obenzyl, —SH, —S$C_{1-6}$alkyl, —S$C_{3-6}$cycloalkyl, —Sphenyl, —Sbenzyl, —CN, —NO$_2$, —N($R^y$)$R^z$ (wherein $R^y$ and $R^z$ are independently selected from H and $C_{1-4}$alkyl; or $R^y$ and $R^z$ may be taken together with the nitrogen of attachment to form a 5-, 6-, or 7-membered monocyclic heterocyclic ring having 1 or 2 additional heteroatom members selected from O, S, —N=, >NH, and >N$C_{1-4}$alkyl, said ring optionally substituted with —$C_{1-4}$alkyl, —OH, —O$C_{1-4}$alkyl, halo, or —COO$C_{1-4}$alkyl), —(C=O)N($R^y$)$R^z$, —(C=O)$C_{1-4}$alkyl, —SCF$_3$, —OCF$_3$, —CF$_3$, —COO$C_{1-4}$alkyl, and —COOH;

or, alternatively $R^3$ and $R^4$ may be taken together with the nitrogen of attachment to form a ring, said ring selected from the group consisting of:

i) a 4-7 membered non-aromatic heterocyclic ring said heterocyclic ring having 0 or 1 additional heteroatom members separated from the nitrogen of attachment by at least one carbon member and selected from O, S, —N=, >NH, and >N$C_{1-4}$alkyl, having 0, 1, or 2 double bonds, having 0, 1, or 2 carbon members which is a carbonyl, having 0, 1, or 2 substituents $R^t$; and ii) a benzo or pyrido fused 4-7 membered non-aromatic heterocyclic ring said heterocyclic ring having 0 or 1 additional heteroatom members separated from the nitrogen of attachment by at least one carbon member and selected from O, S, —N=, >NH, and >N$C_{1-4}$alkyl, having 0 or 1 additional double bonds, having 0, 1, or 2 carbon members which is a carbonyl, and having 0, 1, or 2 substituents $R^t$;

$R^t$ is independently selected from the group consisting of is independently selected from the group consisting of —$C_{1-6}$alkyl, halo, —OH, —O$C_{1-6}$alkyl, —CN, —NO$_2$, —CF$_3$, and —COO$C_{1-4}$alkyl;

and enantiomers, diastereomers, hydrates, solvates and pharmaceutically acceptable salts, esters and amides thereof.

Similarly, isomeric forms of the compounds of formula (I), and of their pharmaceutically acceptable salts, esters, and amides, are encompassed within the present invention, and reference herein to one of such isomeric forms is meant to refer to at least one of such isomeric forms. One of ordinary skill in the art will recognize that compounds according to this invention may exist, for example in a single isomeric form whereas other compounds may exist in the form of a regioisomeric mixture.

The invention also features pharmaceutical compositions containing such compounds and methods of using such compositions in the treatment or prevention of disease states mediated by histamine H$_3$ receptor activity.

The invention also features a pharmaceutical composition comprising a compound of the invention and a pharmaceutically acceptable carrier; and methods of preparing or formulating such compositions. A composition of the invention may further include more than one compound of the invention, or a combination therapy (combination formulation or combination of differently formulated active agents).

The invention also provides methods of treating certain conditions and diseases, each of which methods includes administering a therapeutically effective (or jointly effective) amount of a compound or composition of the invention to a subject in need of such treatment. The disclosed compounds are useful in methods for treating or preventing neurologic disorders including sleep/wake and arousal/vigilance disorders (e.g. insomnia and jet lag), attention deficit hyperactivity disorders (ADHD), learning and memory disorders, cognitive dysfunction, migraine, neurogenic inflammation, dementia, mild cognitive impairment (pre-dementia), Alzheimer's disease, epilepsy, narcolepsy with or without associated cataplexy, cataplexy, disorders of sleep/wake homeostasis, idiopathic somnolence, excessive daytime sleepiness (EDS), circadian rhythm disorders, sleep/fatigue disorders, fatigue, drowsiness associated with sleep apnea, sleep impairment due to perimenopausal hormonal shifts, Parkinson's-related fatigue, MS-related fatigue, depression-related fatigue, chemotherapy-induced fatigue, eating disorders, obesity, motion sickness, vertigo, schizophrenia, substance abuse, bipolar disorders, manic disorders and depression, as well as other histamine H$_3$ receptor mediated disorders such as upper airway allergic response, asthma, itch, nasal congestion and allergic rhinitis in a subject in need thereof. For example, the invention features methods for preventing, inhibiting the progression of, or treating upper airway allergic response, asthma, itch, nasal congestion and allergic rhinitis.

In yet another embodiment, the disclosed compounds may be used in a combination therapy method including administering a jointly effective dose of an H$_3$ antagonist and administering a jointly effective dose of a histamine H$_1$ antagonist, such as loratidine (CLARITIN™), desloratidine (CLARINEX™), fexofenadine (ALLEGRA™) and cetirizine (ZYRTEC™), for the treatment of allergic rhinitis, nasal congestion, and allergic congestion.

In yet another embodiment, the disclosed compounds may be used in a combination therapy method, including administering a jointly effective dose of an H$_3$ antagonist and administering a jointly effective dose of a neurotransmitter re-uptake blocker, such as a selective serotonin re-uptake inhibitor (SSRI), a serotonin-norepinephrine reuptake inhibitor, a noradrenergic reuptake inhibitor, or a non-selective serotonin, dopamine or norepinephrine re-uptake inhibitor, including fluoxetine (PROZAC™), sertraline (ZOLOFT™), paroxetine (PAXIL™) and amitryptyline, for the treatment of depression, mood disorders or schizophrenia. In an alternative embodiment, the disclosed compounds may be used in a combination therapy method, including administering a jointly effective dose of an H$_3$ antagonist and administering a jointly effective dose of modafinil, for example, for the treatment of narcolepsy, excessive daytime sleepiness (EDS), Alzheimer's disease, depression, attention deficit disorders, MS-related fatigue, post-anesthesia grogginess, cognitive impairment, schizophrenia, spasticity associated with cerebral palsy, age-related memory decline, idiopathic somnolence, or jet-lag.

Additional features and advantages of the invention will become apparent from the detailed description and examples below, and the appended claims.

DETAILED DESCRIPTION

Preferably, the A- and B-containing ring is selected from the group consisting of pyridine, pyrazine, and isoxazole.

Preferably, A, $B^1$ and $B^2$ are CH; $B^1$ is N and $B^2$ and A are CH; or A is absent, $B^1$ is CH, and $B^2$ is O.

More preferably, the A- and B-containing ring is pyridine.

More preferably, the A- and B-containing ring is a 3,6-disubstituted pyridine.

More preferably, the A- and B-containing ring is a 2,5-disubstituted pyridine.

More preferably, the A- and B-containing ring is a 2,5-disubstituted pyrazine.

More preferably, the A- and B-containing ring is a 3,5-disubstituted isoxazole.

Even more preferably, A is CH or A is absent.

Even more preferably, $B^1$ is CH or N.

Even more preferably, $B^2$ is CH or O.

Preferably, L is methylene.

Preferably, Q is selected from the group consisting of propylenoxy, ethylenoxy, propyn-1-ylene, butyn-1-ylene, carbonyl, and thiocarbonyl.

Preferably, Q is propylenoxy, butyn-1-ylene, or carbonyl.

Preferably, Q is carbonyl.

Preferably, $R^1$ is independently selected from the group consisting of —H, methyl, ethyl, propyl, isopropyl, butyl, isobutyl, methoxyethyl, hydroxyethyl, piperidinylethyl, morpholinylethyl, pyridylethyl, diethylaminoethyl, propenyl, propargyl, cyclopropyl, cyclopentyl, cyclohexyl, phenyl, benzyl, pyridinyl, pyrrolyl, pyrrolidinyl, piperidinyl, morpholinyl, thiomorpholinyl, and azepanyl.

More preferably, $R^1$ is independently selected from the group consisting of —H, methyl, ethyl, propyl, isopropyl, butyl, isobutyl, methoxyethyl, cyclopropyl, piperidinylethyl, morpholinylethyl, pyridylethyl, and diethylaminoethyl.

Even more preferably, $R^1$ is independently selected from the group consisting of —H, methyl, and methoxyethyl.

Preferably, $R^2$ is independently selected from the group consisting of methyl, ethyl, propyl, isopropyl, butyl, isobutyl, methoxyethyl, hydroxyethyl, piperidinylethyl, morpholinylethyl, pyridylethyl, diethylaminoethyl, propenyl, propargyl, cyclopropyl, cyclopentyl, cyclohexyl, phenyl, benzyl, pyridinyl, pyrrolyl, pyrrolidinyl, piperidinyl, morpholinyl, thiomorpholinyl, and azepanyl.

More preferably, $R^2$ is independently selected from the group consisting of methyl, ethyl, propyl, isopropyl, butyl, isobutyl, methoxyethyl, cyclopropyl, piperidinylethyl, morpholinylethyl, pyridylethyl, and diethylaminoethyl.

Even more preferably, $R^2$ is independently selected from the group consisting of methyl and methoxyethyl.

Preferably, where $R^1$ and $R^2$ are taken together with the nitrogen of attachment to form a ring, said ring is selected from the group consisting of piperidine, morpholine, thiomorpholine, piperazine, and pyrrolidine.

More preferably, $R^1$ and $R^2$ may be taken together with the nitrogen of attachment to form a ring selected from the group consisting of piperidine, morpholine, and piperazine.

In an alternative embodiment, $R^1$ and $R^2$ may be taken together with the nitrogen of attachment to form 4-fluoropiperidine.

Even more preferably, R and $R^2$ may be taken together with the nitrogen of attachment to form a ring selected from the group consisting of piperidine and morpholine.

Preferably, $R^3$ is independently selected from the group consisting of —H, methyl, ethyl, propyl, isopropyl, butyl, isobutyl, methoxyethyl, hydroxyethyl, piperidinylethyl, morpholinylethyl, pyridylethyl, diethylaminoethyl, propenyl, propargyl, cyclopropyl, cyclopentyl, cyclohexyl, phenyl, benzyl, pyridinyl, pyrrolyl, pyrrolidinyl, piperidinyl, morpholinyl, thiomorpholinyl, and azepanyl.

More preferably, $R^3$ is independently selected from the group consisting of —H, methyl, ethyl, propyl, isopropyl, butyl, isobutyl, methoxyethyl, cyclopropyl, piperidinylethyl, morpholinylethyl, pyridylethyl, and diethylaminoethyl.

Even more preferably, $R^3$ is independently selected from the group consisting of —H, methyl, and methoxyethyl.

Preferably, $R^4$ is independently selected from the group consisting of methyl, ethyl, propyl, isopropyl, butyl, isobutyl, methoxyethyl, hydroxyethyl, piperidinylethyl, morpholinylethyl, pyridylethyl, diethylaminoethyl, propenyl, propargyl, cyclopropyl, cyclopentyl, cyclohexyl, phenyl, benzyl, pyridinyl, pyrrolyl, pyrrolidinyl, piperidinyl, morpholinyl, thiomorpholinyl, and azepanyl.

More preferably, $R^4$ is independently selected from the group consisting of methyl, ethyl, propyl, isopropyl, butyl, isobutyl, methoxyethyl, cyclopropyl, piperidinylethyl, morpholinylethyl, pyridylethyl, and diethylaminoethyl.

Even more preferably, $R^4$ is independently selected from the group consisting of methyl and methoxyethyl.

Preferably, where $R^3$ and $R^4$ are taken together with the nitrogen of attachment to form a ring, said ring is selected from the group consisting of piperidine, morpholine, thiomorpholine, piperazine, and pyrrolidine.

More preferably, $R^3$ and $R^4$ may be taken together with the nitrogen of attachment to form a ring selected from the group consisting of piperidine, morpholine, and piperazine.

In an alternative embodiment, $R^3$ and $R^4$ may be taken together with the nitrogen of attachment to form 4-fluoropiperidine.

Even more preferably, $R^3$ and $R^4$ may be taken together with the nitrogen of attachment to form a ring selected from the group consisting of piperidine and piperazine.

Any of the preferred substituents described above that can be optionally further substituted with any of $R^p$, $R^q$, $R^s$, or $R^t$ according to formula (I) are intended to be so optionally substituted.

It is understood that some compounds referred to herein are chiral and/or have geometric isomeric centers, for example E- and Z-isomers. The present invention encompasses all such optical isomers, including stereoisomers and racemic mixtures, diastereomers, and geometric isomers that possess the activity that characterizes the compounds of this invention. Compounds of the invention may exist as single enantiomers, mixtures of enantiomers, or racemic mixtures. In certain embodiments, the absolute configuration of a single enantiomer may be unknown. In addition, certain compounds referred to herein can exist in solvated as well as unsolvated forms. It is understood that this invention encompasses all such solvated and unsolvated forms that possess the activity that characterizes the compounds of this invention.

Compounds according to the present invention that have been modified to be detectable by some analytic technique are also within the scope of this invention. The compounds of the present invention may be labeled with radioactive elements such as $^{125}I$, $^{18}F$, $^{11}C$, $^{64}Cu$, and the like for use in imaging or for radioactive treatment of patients. An example of such compounds is an isotopically labeled compound, such as an $^{18}F$ isotopically labeled compound that may be used as a probe in detection and/or imaging techniques, such as positron emission tomography (PET) and single-photon emission computed tomography (SPECT). Preferably, compounds of the present invention labeled with $^{18}F$ or $^{11}C$ may be used as a positron emission tomography (PET) molecular probe for studying disorders mediated by the histamine $H_3$ receptor and the serotonin transporter. Another example of such compounds is an isotopically labeled compound, such as a deuterium and/or tritium labeled compound that may be used in reaction kinetic studies. The compounds described herein may be reacted with an appropriate functionalized radioactive reagents using conventional chemistry to provide radiolabeled compounds.

Pharmaceutically acceptable salts, esters, and amides include carboxylate salts (e.g., $C_{1-8}$alkyl, $C_{3-8}$cycloalkyl, aryl, $C_{2-10}$heteroaryl, or $C_{2-10}$ non-aromatic heterocyclic), amino addition salts, acid addition salts, esters, and amides that are within a reasonable benefit/risk ratio, pharmacologically effective and suitable for contact with the tissues of patients without undue toxicity, irritation, or allergic response. Representative salts for compounds of formula (I) displaying basic functionality include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. Representative addition salts for compounds of formula (I) displaying acidic functionality are those that form non-toxic base salts with such compounds. These salts may include alkali metal and alkali earth cations such as sodium, potassium, calcium, and magnesium, as well as non-toxic ammonium, quaternary ammonium, and amine cations such as tetramethyl ammonium, methylammonium, trimethylammonium, and ethylammonium. See example, S. M. Berge, et al., "Pharmaceutical Salts," J. Pharm. Sci., 1977, 66:1-19, which is incorporated herein by reference.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound that may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985. In addition to salts, the invention provides the esters, amides, and other protected or derivatized forms of the described compounds.

Representative pharmaceutically acceptable amides of the invention include those derived from ammonia, primary $C_{1-6}$alkyl amines and secondary di($C_{1-6}$alkyl) amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$alkyl primary amines, and di($C_{1-2}$alkyl)amines. Representative pharmaceutically acceptable esters of the invention include $C_{1-7}$alkyl, $C_{5-7}$cycloalkyl, phenyl, and phenyl($C_{1-6}$)alkyl esters. Preferred esters include ethyl esters.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound that may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985. In addition to salts, the invention provides the esters, amides, and other protected or derivatized forms of the described compounds.

Preferred compounds of the present invention are selected from the group consisting of:

| EX | Compound Name |
|---|---|
| 1 | (4-Isopropyl-piperazin-1-yl)-(6-piperidin-1-ylmethyl-pyridin-3-yl)-methanone; |
| 2 | (4-Isopropyl-piperazin-1-yl)-(6-morpholin-4-ylmethyl-pyridin-3-yl)-methanone; |
| 3 | (4-Isopropyl-piperazin-1-yl)-(5-piperidin-1-ylmethyl-pyridin-2-yl)-methanone; |
| 4 | 2-Piperdin-1-ylmethyl-5-(3-piperdin-1-yl-propoxy)-pyridine; |
| 5 | 4-[5-(3-Piperidin-1-yl-propoxy)-pyridin-2-ylmethyl]-morpholine; |
| 6 | 5-Piperidin-1-ylmethyl-2-(3-piperidin-1-yl-propoxy)-pyridine; |
| 7 | 4-[6-(3-Piperidin-1-yl-propoxy)-pyridin-3-ylmethyl]-morpholine; |
| 8 | 2-(4-Piperidin-1-yl-but-1-ynyl)-5-piperidin-1-ylmethyl-pyridine; |
| 9 | (4-Isopropyl-piperazin-1-yl)-[6-(2-piperidin-1-yl-ethylamino)-pyridin-3-yl]-methanone; |
| 10 | (4-Isopropyl-piperazin-1-yl)-[6-(2-morpholin-4-yl-ethylamino)-pyridin-3-yl]-methanone; |
| 11 | (4-Isopropyl-piperazin-1-yl)-[6-(2-pyridin-2-yl-ethylamino)-pyridin-3-yl]-methanone; |
| 12 | {6-[(2-Diethylamino-ethyl)-methyl-amino]-pyridin-3-yl}-(4-isopropyl-piperazin-1-yl)-methanone; |
| 13 | (4-Isopropyl-piperazin-1-yl)-[6-(4-isopropyl-piperazin-1-yl)-pyridin-3-yl]-methanone; |
| 14 | 4-[5-(4-Isopropyl-piperazine-1-carbonyl)-pyridin-2-yl]-piperazine-1-carboxylic acid ethyl ester; |
| 15 | (4-Isopropyl-piperazin-1-yl)-[6-(4-methyl-piperazin-1-yl)-pyridin-3-yl]-methanone; |
| 16 | (4-Isopropyl-piperazin-1-yl)-[2-(2-piperidin-1-yl-ethylamino)-pyridin-4-yl]-methanone; |
| 17 | (4-Isopropyl-piperazin-1-yl)-[2-(2-piperidin-1-yl-ethylamino)-pyridin-3-yl]-methanone; |
| 18 | 3-(4-Piperidin-1-yl-but-1-ynyl)-5-piperidin-1-ylmethyl-pyridine; |
| 19 | 4-[5-(4-Piperidin-1-yl-but-1-ynyl)-pyridin-3-ylmethyl]-morpholine; |
| 20 | 2-(4-Piperidin-1-yl-but-1-ynyl)-6-piperidin-1-ylmethyl-pyridine; |
| 21 | 4-[6-(4-Piperidin-1-yl-but-1-ynyl)-pyridin-2-ylmethyl]-morpholine; |
| 22 | (2-Methoxy-ethyl)-[6-(4-piperidin-1-yl-but-1-ynyl)-pyridin-2-ylmethyl]-amine; |
| 23 | (4-Isopropyl-piperazin-1-yl)-(5-piperidin-1-ylmethyl-pyrazin-2-yl)-methanone; |
| 24 | (4-Isopropyl-piperazin-1-yl)-(5-morpholin-4-ylmethyl-pyrazin-2-yl)-methanone; |
| 25 | 4-[3-(3-Piperidin-1-yl-propoxy)-isoxazol-5-ylmethyl]-piperidine; |
| 26 | 4-[3-(3-Piperidin-1-yl-propoxy)-isoxazol-5-ylmethyl]-morpholine; |
| 27 | (2-Methoxy-ethyl)-[3-(3-piperidin-1-yl-propoxy)-isoxazol-5-ylmethyl]-amine; and |
| 28 | (4-Isopropyl-piperazin-1-yl)-(6-piperidin-1-ylmethyl-pyridin-3-yl)-methanethione. |

In a preferred embodiment, compounds of the present invention are selected from the group consisting of:

| EX | Compound Name |
|---|---|
| 1 | (4-Isopropyl-piperazin-1-yl)-(6-piperidin-1-ylmethyl-pyridin-3-yl)-methanone; |
| 2 | (4-Isopropyl-piperazin-1-yl)-(6-morpholin-4-ylmethyl-pyridin-3-yl)-methanone; |
| 3 | (4-Isopropyl-piperazin-1-yl)-(5-piperidin-1-ylmethyl-pyridin-2-yl)-methanone; |
| 4 | 2-Piperdin-1-ylmethyl-5-(3-piperdin-1-yl-propoxy)-pyridine; |
| 5 | 4-[5-(3-Piperidin-1-yl-propoxy)-pyridin-2-ylmethyl]-morpholine; |
| 8 | 2-(4-Piperidin-1-yl-but-1-ynyl)-5-piperidin-1-ylmethyl-pyridine; |
| 9 | (4-Isopropyl-piperazin-1-yl)-[6-(2-piperidin-1-yl-ethylamino)-pyridin-3-yl]-methanone; |
| 10 | (4-Isopropyl-piperazin-1-yl)-[6-(2-morpholin-4-yl-ethylamino)-pyridin-3-yl]-methanone; |
| 12 | {6-[(2-Diethylamino-ethyl)-methyl-amino]-pyridin-3-yl}-(4-isopropyl-piperazin-1-yl)-methanone; |
| 13 | (4-Isopropyl-piperazin-1-yl)-[6-(4-isopropyl-piperazin-1-yl)-pyridin-3-yl]-methanone; |

-continued

| EX | Compound Name |
|---|---|
| 15 | (4-Isopropyl-piperazin-1-yl)-[6-(4-methyl-piperazin-1-yl)-pyridin-3-yl]-methanone; |
| 16 | (4-Isopropyl-piperazin-1-yl)-[2-(2-piperidin-1-yl-ethylamino)-pyridin-4-yl]-methanone; |
| 18 | 3-(4-Piperidin-1-yl-but-1-ynyl)-5-piperidin-1-ylmethyl-pyridine; |
| 19 | 4-[5-(4-Piperidin-1-yl-but-1-ynyl)-pyridin-3-ylmethyl]-morpholine; |
| 20 | 2-(4-Piperidin-1-yl-but-1-ynyl)-6-piperidin-1-ylmethyl-pyridine; |
| 21 | 4-[6-(4-Piperidin-1-yl-but-1-ynyl)-pyridin-2-ylmethyl]-morpholine; |
| 22 | (2-Methoxy-ethyl)-[6-(4-piperidin-1-yl-but-1-ynyl)-pyridin-2-ylmethyl]-amine; |
| 23 | (4-Isopropyl-piperazin-1-yl)-(5-piperidin-1-ylmethyl-pyrazin-2-yl)-methanone; |
| 24 | (4-Isopropyl-piperazin-1-yl)-(5-morpholin-4-ylmethyl-pyrazin-2-yl)-methanone; |
| 25 | 4-[3-(3-Piperidin-1-yl-propoxy)-isoxazol-5-ylmethyl]-piperidine; and |
| 28 | (4-Isopropyl-piperazin-1-yl)-(6-piperidin-1-ylmethyl-pyridin-3-yl)-methanethione. |

In another preferred embodiment, compounds of the present invention are selected from the group consisting of:

| EX | Compound Name |
|---|---|
| 1 | (4-Isopropyl-piperazin-1-yl)-(6-piperidin-1-ylmethyl-pyridin-3-yl)-methanone; |
| 3 | (4-Isopropyl-piperazin-1-yl)-(5-piperidin-1-ylmethyl-pyridin-2-yl)-methanone; |
| 4 | 2-Piperdin-1-ylmethyl-5-(3-piperdin-1-yl-propoxy)-pyridine; |
| 8 | 2-(4-Piperidin-1-yl-but-1-ynyl)-5-piperidin-1-ylmethyl-pyridine; |
| 9 | (4-Isopropyl-piperazin-1-yl)-[6-(2-piperidin-1-yl-ethylamino)-pyridin-3-yl]-methanone; |
| 12 | {6-[(2-Diethylamino-ethyl)-methyl-amino]-pyridin-3-yl}-(4-isopropyl-piperazin-1-yl)-methanone; |
| 13 | (4-Isopropyl-piperazin-1-yl)-[6-(4-isopropyl-piperazin-1-yl)-pyridin-3-yl]-methanone; |
| 15 | (4-Isopropyl-piperazin-1-yl)-[6-(4-methyl-piperazin-1-yl)-pyridin-3-yl]-methanone; |
| 16 | (4-Isopropyl-piperazin-1-yl)-[2-(2-piperidin-1-yl-ethylamino)-pyridin-4-yl]-methanone; |
| 18 | 3-(4-Piperidin-1-yl-but-1-ynyl)-5-piperidin-1-ylmethyl-pyridine; |
| 20 | 2-(4-Piperidin-1-yl-but-1-ynyl)-6-piperidin-1-ylmethyl-pyridine; |
| 23 | (4-Isopropyl-piperazin-1-yl)-(5-piperidin-1-ylmethyl-pyrazin-2-yl)-methanone; |
| 25 | 4-[3-(3-Piperidin-1-yl-propoxy)-isoxazol-5-ylmethyl]-piperidine; and |
| 28 | (4-Isopropyl-piperazin-1-yl)-(6-piperidin-1-ylmethyl-pyridin-3-yl)-methanethione. |

The features and advantages of the invention are apparent to one of ordinary skill in the art. Based on this disclosure, including the summary, detailed description, background, examples, and claims, one of ordinary skill in the art will be able to make modifications and adaptations to various conditions and usages. Publications described herein are incorporated by reference in their entirety. Where chemical symbols are used, it is understood that they are read from left to right, and that otherwise their spatial orientation has no significance.

The compounds as described above may be made according to processes within the skill of the art and/or that are described in the schemes and examples that follow. To obtain the various compounds herein, starting materials may be employed that carry the ultimately desired substituents though the reaction scheme with or without protection as appropriate. This may be achieved by means of conventional protecting groups, such as those described in "Protective Groups in Organic Chemistry", ed. J. F. W. McOmie, Plenum Press, 1973; and T. W. Greene & P. G. M. Wuts, "Protective Groups in Organic Synthesis", 3$^{rd}$ ed., John Wiley & Sons, 1999. The protecting groups may be removed at a convenient subsequent stage using methods known from the art. Alternatively, it may be necessary to employ, in the place of the ultimately desired substituent, a suitable group that may be carried through the reaction scheme and replaced as appropriate with the desired substituent. Such compounds, precursors, or prodrugs are also within the scope of the invention.

The compounds as described above may be made according to Schemes A-G below. Persons skilled in the art will recognize that certain compounds are more advantageously produced by one scheme as compared to the other.

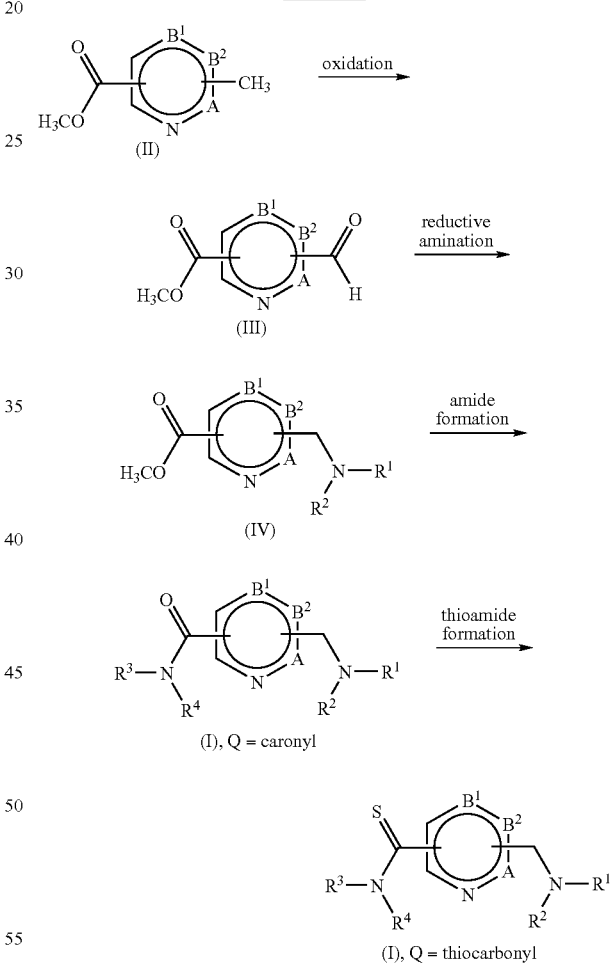

Compounds of formula (I) may be prepared as shown in Scheme A, with the following notes and additions. Commercially available heterocyclic ester derivatives (II) may be oxidized to the corresponding aldehydes (III) at a benzylic methyl position under conditions such as I$_2$, t-butyl chloride, TFA, and DMSO. This transformation may also be accomplished in two steps by dibromination of the methyl substituent using N-bromosuccinimide and dibenzoyl peroxide, followed by reaction of the dibromide with silver nitrate in ethanol with heating to form the aldehyde. The aldehyde functionality can then be reacted under conditions of reductive amination to provide compounds of formula (IV). The aldehyde can be treated with a suitable amine, with or without the addition of an activating agent such as a protic or Lewis acid, and with an appropriate reducing agent such as sodium triacetoxyborohydride. The aldehyde may alternatively be reduced to an alcohol, converted to a leaving group such as a chloride and displaced with an appropriate amine as shown below in Scheme G. The chloride could also be displaced with cyanide anion, and the resulting nitrile reduced to homologate the linker by one additional carbon. Alternatively, the aldehyde may be reacted using Horner-Emmons chemistry followed by hydrogenation of the double bond to introduce an alkyl chain containing an additional two carbons. The ester can be converted to a range of amides of formula (I) using a primary or secondary amine, in the. presence of a Lewis acid activating agent such as $MgBr_2$. The carboxamide may be converted to its corresponding thioamides of formula (I) by treatment with $P_2S_5$ or Lawesson's reagent.

Scheme B.

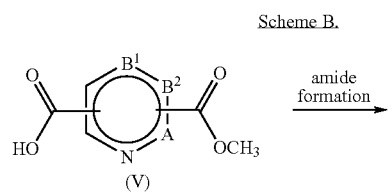

(V)

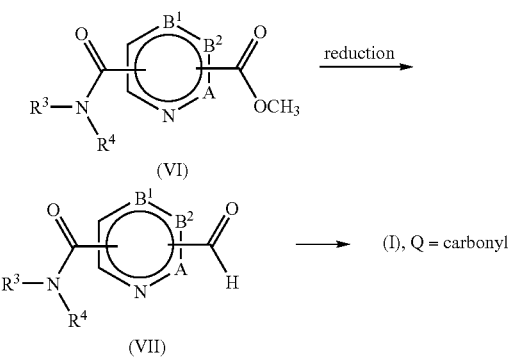

Compounds of formula (I) may also be prepared as shown in Scheme B, with the following notes and additions. Acid derivatives (V) can be converted to their corresponding amides (VI) under standard peptide coupling conditions, with an appropriate primary or secondary amine, in the presence of coupling agents such as 1-hydroxybenzotriazole hydrate (HOBt), 1-[3-(dimethylamino)propyl]-3-ethylcarbodiimide HCl (EDCI), and N-methylmorpholine. Selective reduction of the ester group to the aldehyde (VII) may be performed with DIBAL-H, or a two-step sequence can be employed wherein the ester is reduced to the alcohol with a hydride agent such as $LiAlH(otBu)_3$ or $NaBH_4$, followed by oxidation to the aldehyde with $MnO_2$, Dess-Martin periodinane, or Swern oxidation. The aldehyde would be converted into compounds of formula (I) where Q is carbonyl or thiocarbonyl, using the methods described for Scheme A.

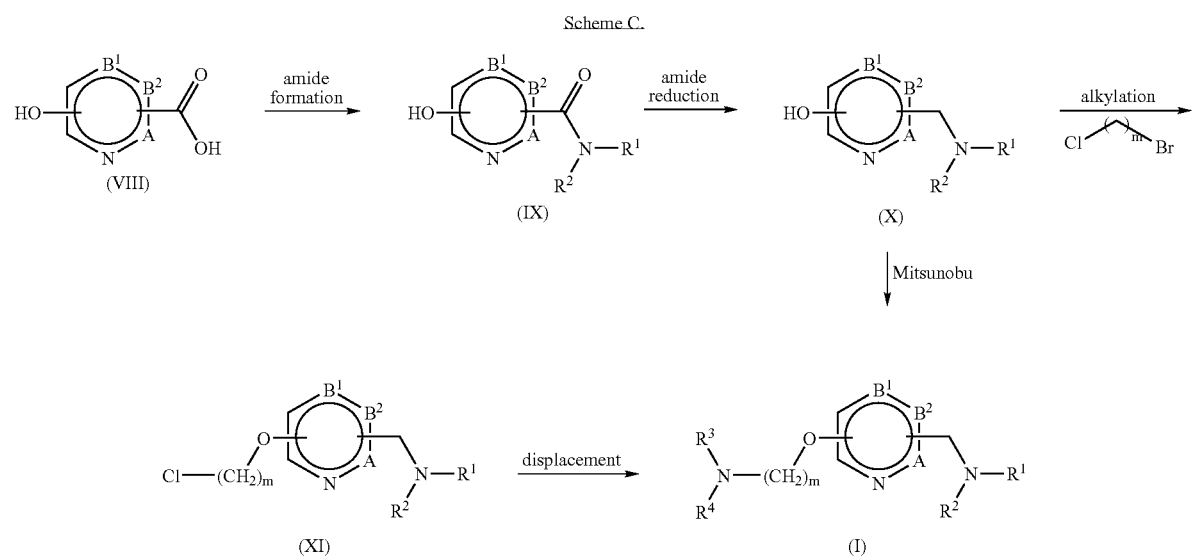

Alternatively, compounds of formula (I) may also be produced as shown in Scheme C, with the following notes and additions. Heterocyclic hydroxy acids (VIII) may be reacted under peptide coupling conditions with a primary or secondary amine as described above to form amides (IX). The amide functionality may be reduced to the corresponding amine (X) using an appropriate reducing agent such as borane-dimethylsulfide. The hydroxyl functionality may be alkylated with a suitable alkylating agent to install the hydrocarbon linker (XI), such as 1-bromo-3-chloropropane or 1-bromo-4-chloropropane, in the presence of a suitable base such as $K_2CO_3$. To achieve the desired O-regioselectivity of the alkylation, $Ag_2CO_3$ may be used. The tethered leaving group may be displaced with a primary or secondary amine, with or without the addition of catalytic KI, and in the presence of a suitable base such as $Na_2CO_3$. Alternatively, compounds of formula (X) may be converted directly to compounds of formula (I) under Mitsunobu conditions with an amine-functionalized alcohol such as 3-piperidin-1-ylpropanol, standard or polymer-supported triphenylphosphine, and di-t-butyl azodicarboxylate, in a solvent such as dichloromethane.

Compounds of formula (I) may also be prepared as decribed in Scheme D, with the following notes and additions. Compounds of formula (XII) where X is bromide may be converted to bromo aldehydes (XIII) by treatment with an organolithium reagent such as n-BuLi, and quenching the lithium anion with DMF. The intermediate lithium species may be converted to corresponding Grignard reagent in situ via treatment with n-BuMgCl. Bromo aldehydes can be prepared from commercially available carboxylic acids using methods known to one skilled in the art. The aldehydes (XIII) can be transformed into amines (XIV) using reductive amination conditions as described above. Alternatively, alcohols of formula (X) may be converted to the corresponding triflates (XIV, X=OTf) using reagents such as N-phenyltrifluoromethane-sulfonimide or triflic anhydride, in the presence of a tertiary amine base such as triethylamine. The triflates and bromides may be coupled, typically under conditions of palladium catalysis, with terminal alkynes suitably functionalized with an amine substituent, such as 1-but-3-ynyl-piperidine (Turner, S. C. et al. Bioorg. Med. Chem. Lett. 2003, 13(13):2131-2136) in the presence of a palladium catalyst such as $(PPh_3)_2PdCl_2$, with or without additives such as CuI, triphenylphosphine, and triethylamine, to form compounds of formula (I).

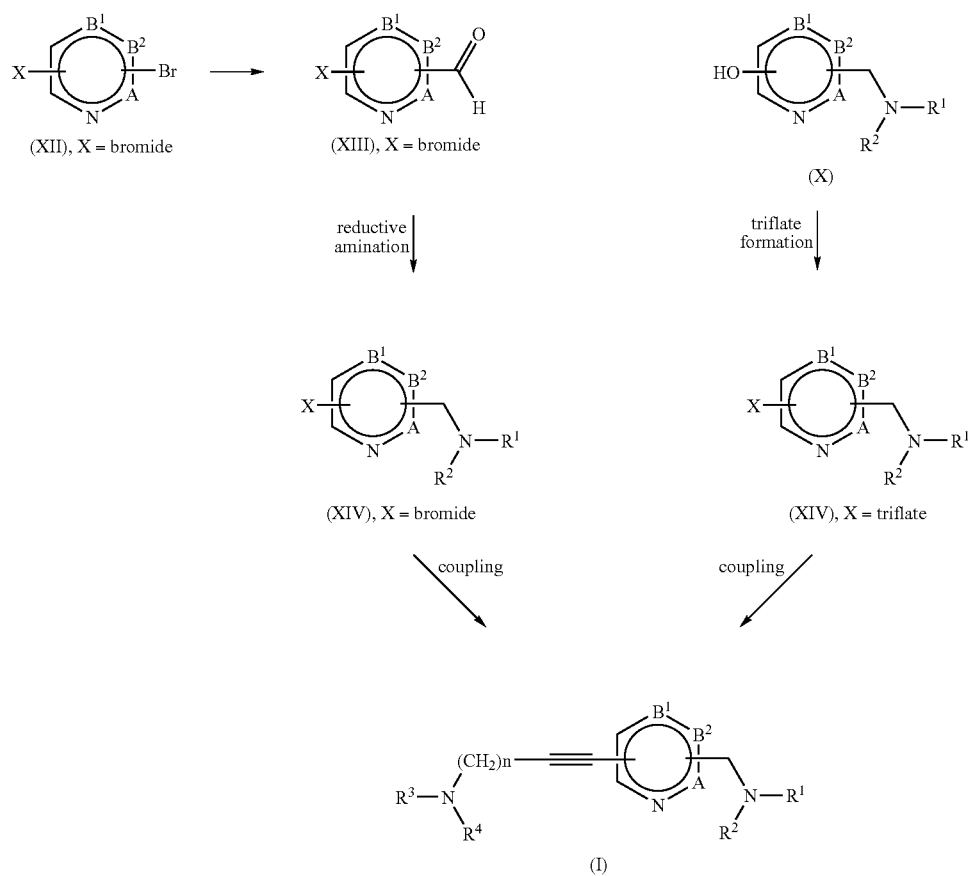

Scheme E.

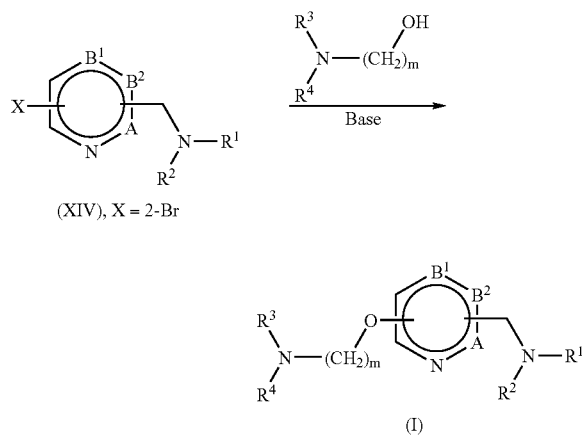

Compounds of formula (I) may also be prepared as shown in Scheme E, with the following notes and additions. 2-Bromo substituted heterocycles of formula (XIV), prepared as described in Scheme D, may be converted to compounds of formula (I) by displacement with a suitable alkoxide reagent, formed by reaction of the desired subunit such as 3-piperidin-1-yl-propan-1-ol and the bromide in the presence of a strong base such as sodium hydride.

Scheme F.

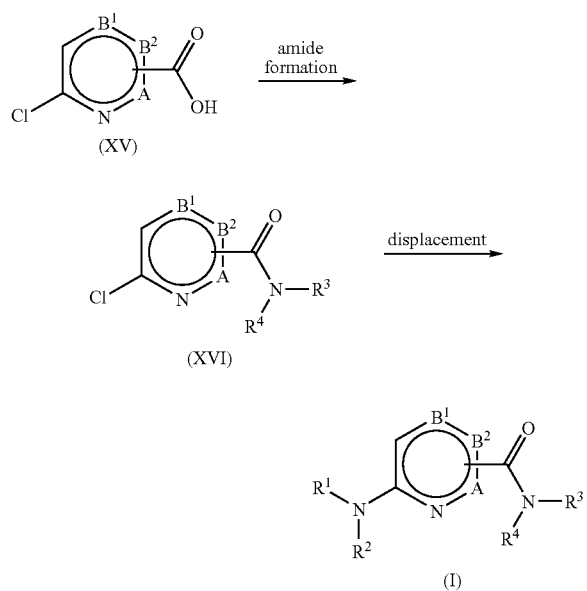

Compounds of formula (I) may also be prepared as shown in Scheme F, with the following notes and additions. Heterocyclic acids (XV) with a 2-chloro substituent may be converted to the corresponding amides (XVI) as described above. The chloride may be displaced by an appropriate primary or secondary amine, with or without heating, in a solvent such as n-BuOH, to form compounds of formula (I) where L is absent.

Scheme G.

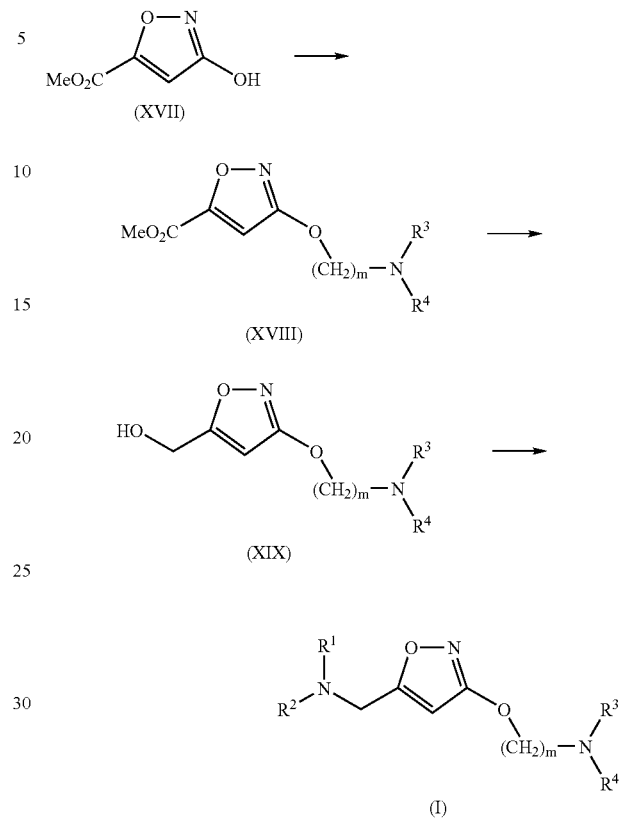

Referring to Scheme G, there are the following notes and additions. The free hydroxyl group in isoxazoles (XVII) may be alkylated under Mitsunobu conditions, using a suitably functionalized amino alcohol such as 3-piperidin-1-yl-propan-1-ol, polymer-supported triphenylphosphine, and di-t-butyl azodicarboxylate, in a solvent such as dichloromethane. The alcohol could also be converted to amine (XVIII) using alkylation and displacement steps described above. The ester functionality may be reduced to form alcohols of formula (XIX). The alcohol may be converted to the corresponding chloride with thionyl chloride, and subsequently displaced with a suitable primary or secondary amine to form compounds of formula (I). Alternatively, the alcohol may be oxidized to the corresponding aldehyde and transformed under conditions of reductive amination as described above.

Compounds prepared according to the schemes described above may be obtained as single enantiomers, mixtures of enantiomers, or racemic mixtures. Where racemic (1:1) and non-racemic (not 1:1) mixtures of enantiomers are obtained, single enantiomers may be isolated using conventional separation methods known to one skilled in the art. Particularly useful separation methods may include chiral chromatography, recrystallization, resolution, diastereomeric salt formation, or derivatization into diastereomeric adducts followed by separation.

The compounds of the present invention are modulators of the histamine $H_3$ receptor, and as such, the compounds are useful in the treatment of histamine $H_3$-mediated disease states.

Compounds of the present invention may be administered in pharmaceutical compositions to treat patients (humans and other mammals) with disorders mediated by the $H_3$ receptor. The disclosed compounds, alone or in combination (with, for example, a histamine $H_1$ receptor antagonist), are useful for treating or preventing neurologic disorders including sleep/wake and arousal/vigilance disorders (e.g. insomnia and jet lag), attention deficit hyperactivity disorders (ADHD), learning and memory disorders, cognitive dysfunction, migraine, neurogenic inflammation, dementia, mild cognitive impairment (pre-dementia), Alzheimer's disease, epilepsy, narcolepsy with or without associated cataplexy, cataplexy, disorders of sleep/wake homeostasis, idiopathic somnolence, excessive daytime sleepiness (EDS), circadian rhythm disorders, sleep/fatigue disorders, fatigue, drowsiness associated with sleep apnea, sleep impairment due to perimenopausal hormonal shifts, Parkinson's-related fatigue, MS-related fatigue, depression-related fatigue, chemotherapy-induced fatigue, eating disorders, obesity, motion sickness, vertigo, schizophrenia, substance abuse, bipolar disorders, manic disorders and depression, as well as other histamine $H_3$ receptor mediated disorders such as upper airway allergic response, asthma, itch, nasal congestion and allergic rhinitis in a subject in need thereof. Excessive daytime sleepiness (EDS) may occur with or without associated sleep apnea, shift work, fibromyalgia, MS, and the like.

The present invention also provides pharmaceutical compositions comprising one or more compounds of this invention in association with a pharmaceutically acceptable carrier and optionally additional pharmaceutical agents such as $H_1$ antagonists, SSRIs, or modafinil. The pharmaceutical compositions can be prepared using conventional pharmaceutical excipients and compounding techniques known to those skilled in the art of preparing dosage forms. It is anticipated that the compounds of the invention can be administered by oral, parenteral, rectal, topical, or ocular routes, or by inhalation. Preparations may also be designed to give slow release of the active ingredient. The preparation may be in the form of tablets, capsules, sachets, vials, powders, granules, lozenges, powders for reconstitution, liquid preparations, or suppositories. Preferably, compounds may be administered by intravenous infusion or topical administration, but more preferably by oral administration.

For oral administration, the compounds of the invention can be provided in the form of tablets or capsules, or as a solution, emulsion, or suspension. Tablets for oral use may include the active ingredient mixed with pharmaceutically acceptable excipients such as inert diluents, disintegrating agents, binding agents, lubricating agents, sweetening agents, flavoring agents, coloring agents and preservatives agents. Suitable inert fillers include sodium and calcium carbonate, sodium and calcium phosphate, lactose, starch, sugar, glucose, methyl cellulose, magnesium stearate, mannitol, sorbitol, and the like; typical liquid oral excipients include ethanol, glycerol, water and the like. Starch, polyvinyl-pyrrolidone, sodium starch glycolate, microcrystalline cellulose, and alginic acid are suitable disintegrating agents. Binding agents may include starch and gelatin. The lubricating agent, if present, will generally be magnesium stearate, stearic acid or talc. If desired, the tablets may be coated with a material such as glyceryl monostearate or glyceryl distearate to delay absorption in the gastrointestinal tract, or may be coated with an enteric coating. Capsules for oral use include hard gelatin capsules in which the active ingredient is mixed with a solid, semi-solid, or liquid diluent, and soft gelatin capsules wherein the active ingredient is mixed with water, an oil such as peanut oil or olive oil, liquid paraffin, a mixture of mono and di-glycerides of short chain fatty acids, polyethylene glycol 400, or propylene glycol.

Liquids for oral administration may be suspensions, solutions, emulsions or syrups or may be presented as a dry product for reconstitution with water or other suitable vehicles before use. Compositions of such liquid may contain pharmaceutically-acceptable excipients such as suspending agents (for example, sorbitol, methyl cellulose, sodium alginate, gelatin, hydroxyethylcellulose, carboxymethylcellulose, aluminium stearate gel and the like); non-aqueous vehicles, which include oils (for example, almond oil or fractionated coconut oil), propylene glycol, ethyl alcohol or water; preservatives (for example, methyl or propyl p-hydroxybenzoate or sorbic acid); wetting agents such as lecithin; and, if needed, flavoring or coloring agents.

The compounds of this invention may also be administered by non-oral routes. The compositions may be formulated for rectal administration as a suppository. For parenteral use, including intravenous, intramuscular, intraperitoneal, or subcutaneous routes, the compounds of the invention will generally be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit dose form such as ampules or disposable injection devices, in multi-dose forms such as vials from which the appropriate dose may be withdrawn, or in a solid form or pre-concentrate that can be used to prepare an injectable formulation. Another mode of administration of the compounds of the invention may utilize a patch formulation to affect transdermal delivery. The compounds of this invention may also be administered by inhalation, via the nasal or oral routes using a spray formulation consisting of the compound of the invention and a suitable carrier.

Effective doses of the compounds of the present invention may be ascertained by conventional methods. The specific dosage level required for any particular patient will depend on a number of factors, including severity of the condition being treated, the route of administration, and the weight of the patient. In general, however, it is anticipated that the daily dose (whether administered as a single dose or as divided doses) will be in the range 0.01 to 1000 mg per day, more usually from 1 to 500 mg per day, and most usually from 10 to 200 mg per day. Expressed as dosage per unit body weight, a typical dose will be expected to be between 0.0001 mg/kg and 15 mg/kg, especially between 0.01 mg/kg and 7 mg/kg, and most especially between 0.15 mg/kg and 2.5 mg/kg.

Preferably, oral doses range from about 0.05 to 200 mg/kg, daily, taken in 1 to 4 separate doses. Some compounds of the invention may be orally dosed in the range of about 0.05 to about 50 mg/kg daily, others may be dosed at 0.05 to about 20 mg/kg daily, while still others may be dosed at 0.1 to about 10 mg/kg daily. Infusion doses can range from about 1 to 1000 μg/kg/min of inhibitor, admixed with a pharmaceutical carrier over a period ranging from several minutes to several days. For topical administration compounds of the present invention may be mixed with a pharmaceutical carrier at a concentration of about 0.1% to about 10% of drug to vehicle.

The disclosed compounds are useful in combination with other therapeutic agents, including $H_1$ receptor antagonists, $H_2$ receptor antagonists, and neurotransmitter modulators such as SSRIs, serotonin-norepinephrine reuptake inhibitors, noradrenergic reuptake inhibitors, non-selective serotonin reuptake inhibitors (NSSRIs), or other neuroactive agents such as modafinil.

Methods are known in the art for determining effective doses for therapeutic and prophylactic purposes for the disclosed pharmaceutical compositions or the disclosed drug combinations, whether or not formulated in the same composition. For therapeutic purposes, the term "jointly effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "jointly effective amount" refers to that amount of each active compound or pharmaceutical agent, alone or in combination, that inhibits in a subject the onset or progression of a disorder as being sought by a researcher, veterinarian, medical doctor or other clinician, the delaying of which disorder is mediated, at least in part, by the modulation of one or more histamine receptors. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both drugs are administered in an amount that is sub-therapeutic or sub-prophylactic if administered alone, but are therapeutic or prophylactic when administered together. Combinations of three or more drugs are analogously possible. Methods of combination therapy include co-administration of a single formulation containing all active agents; essentially contemporaneous administration of more than one formulation; and administration of two or more active agents separately formulated.

EXAMPLES

In order to illustrate the invention, the following examples are included. These examples do not limit the invention. They are only meant to suggest a method of practicing the invention. Those skilled in the art may find other methods of practicing the invention, which are obvious to them. However, those methods are deemed to be within the scope of this invention.

Protocol for Preparative Reversed-Phase HPLC

| Gilson ® instrument | |
| --- | --- |
| Column: | YMC-Pack ODS-A, 5 μm, 75 × 30 mm |
| Flow Rate: | 10 mL/min |
| Detection: | λ = 220 & 254 nm |
| Gradient (acetonitrile/H$_2$O, 0.05% trifluoracetic acid) | |
| 1) 0.0 min | 20% acetonitrile/80% H$_2$O |
| 2) 20.0 min | 99% acetonitrile/1% H$_2$O |

Protocol for HPLC (Reversed-Phase)

| Hewlett Packard Series 1100 | |
| --- | --- |
| Column: | Agilent ZORBAX ® C8, 5 μ, 4.6 × 150 mm |
| Flow rate: | 1 mL/min |
| Detection: | λ = 200 & 254 nm |
| Gradient(acetonitrile/H$_2$O, 0.05% trifluoroacetic acid) | |
| 1) 0.0 min | 1% acetonitrile/99% H$_2$O |
| 2) 8.0 min | 99% acetonitrile/1% H$_2$O |

Mass spectra were obtained on an Agilent series 1100 MSD using electrospray ionization (ESI) in either positive or negative modes as indicated.

NMR spectra were obtained on either a Bruker model DPX400 (400 MHz) or DPX500 (500 MHz) spectrometer. The format of the $^1$H NMR data below is: chemical shift in ppm down field of the tetramethylsilane reference (multiplicity, coupling constant J in Hz, integration).

Example 1

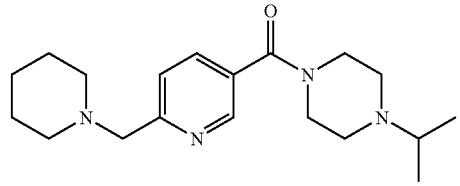

(4-Isopropyl-piperazin-1-yl)-(6-piperidin-1-ylmethyl-pyridin-3-yl)-methanone

Step A. 6-Formyl-nicotinic acid methyl ester.

A solution of 6-methyl nicotinic acid methyl ester (1.00 g, 6.62 mmol), iodine (1.68 g, 6.62 mmol), 2-iodo-2-methylpropane (0.478.g, 2.60 mmol) and trifluoroacetic acid (2.26 g, 19.8 mmol) in anhydrous DMSO was heated for 3 h at 160° C. The reaction mixture was cooled to room temperature (rt) and treated with 1 N aq. Na$_2$S$_2$O$_3$ (50 mL). The reaction mixture was adjusted to pH 10 with 1 N aq. NaHCO$_3$. The reaction mixture was extracted with ethyl acetate (3×100 mL). The combined organic phases were dried over anhydrous Na$_2$SO$_4$, filtered, and concentrated. Chromatography of the residue (SiO$_2$; 0-3% EtOH:DCM) gave the title compound as a solid (0.506 g, 46%).

Step B. 6-Piperidin-1-ylmethyl-nicotinic acid methyl ester.

To a solution of 6-formyl-nicotinic acid methyl ester (0.200 g, 1.21 mmol) and piperidine (0.14 mL, 1.33 mmol) in DCM (15 mL) was added NaB(OAc)$_3$H (0.380 g, 1.80 mmol). After 18 h, the reaction was diluted with 1 N NaOH (10 mL) and extracted with DCM (2×50 mL). The organic layers were combined, dried (Na$_2$SO$_4$), and concentrated. Chromatography of the residue (SiO$_2$; 1-3% 2 M NH$_3$ in MeOH/DCM) gave the title compound as an oil (0.210 g, 74%).

Step C. (4-Isopropyl-piperazin-1-yl)-(6-piperidin-1-ylmethyl-pyridin-3-yl)-methanone.

A solution of 6-piperidin-1-ylmethyl-nicotinic acid methyl ester (0.300 g, 1.28 mmol), and MgBr$_2$.OEt$_2$ (0.900 g, 3.84 mmol) in THF (15 mL) was stirred for 15 min. A solution of 1-isopropyl-piperazine (0.325 g, 2.56 mmol) in THF (2 mL) was then added to the reaction drop-wise and the mixture was heated at reflux for 48 h. The reaction mixture was cooled to rt, concentrated, treated with 1 N aq. NaHCO$_3$ (50 mL), and extracted with ethyl acetate (3×50 mL). The organic layers were combined, dried (Na$_2$SO$_4$), and concentrated. Chromatography of the residue (SiO$_2$; 3-6% 2 M NH$_3$ in MeOH/DCM) gave the title compound as an oil (0.297 g, 70%). MS (ESI): exact mass calcd. for C$_{19}$H$_{30}$N$_4$O, 330.2; m/z found, 331.2 [M+H]$^+$. $^1$H NMR (400 MHz, CDCl$_3$): 8.55 (d, J=2.2, 1H), 7.87 (dd, J=7.8, 2.0, 1H), 7.62 (d, J=7.6, 1H), 3.78 (br s, 2H), 3.67 (s, 2H), 3.48 (br s, 2H), 2.77-2.73 (m, 1H), 2.65-2.48 (m, 8H), 1.65-1.59 (m, 4H), 1.49-1.48 (m, 2H), 1.09 (d, J=6.6, 6H).

Example 2

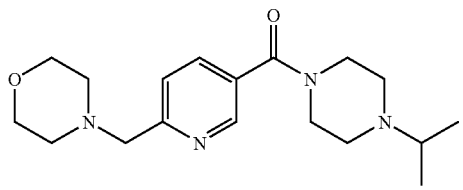

(4-Isopropyl-piperazin-1-yl)-(6-morpholin-4-ylmethyl-pyridin-3-yl)-methanone

The title compound was synthesized in a similar manner as Example 1 substituting morpholine for piperidine in step B. MS (ESI): exact mass calcd. for C$_{18}$H$_{28}$N$_4$O$_2$, 332.2; m/z found, 333.2 [M+H]$^+$. $^1$H NMR (400 MHz, CDCl$_3$): 8.60 (d, J=2.3, 1H), 7.72 (dd, J=7.8, 2.3, 1H), 7.48 (d, J=7.8, 1H), 3.79-3.72 (m, 6H), 3.67 (s, 2H), 3.44 (br s, 2H), 2.75-2.72 (m, 1H), 2.60 (br s, 2H), 2.52-2.48 (m, 6H), 1.05 (d, J=6.6, 6H).

Example 3

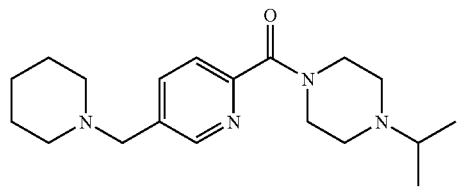

(4-Isopropyl-piperazin-1-yl)-(5-piperidin-1-ylmethyl-pyridin-2-yl)-methanone

Step A. 6-(4-Isopropyl-piperazine-1-carbonyl)-nicotinic acid methyl ester.

To a solution of pyridine-2,5-dicarboxylic acid 5-methyl ester (1.00 g, 5.50 mmol) and 1-isopropyl-piperazine dihydrochloride (1.20 g, 6.10 mmol) in DCM (100 mL) was added 1-hydroxybenzotriazole hydrate (HOBt, 1.10 g, 8.30 mmol), 1-[3-(dimethylamino)propyl]-3-ethylcarbodiimide hydrochloride (EDC, 1.60 g, 8.30 mmol), and N-methyl morpholine (2.9 mL, 27.0 mmol). After 18 h, the reaction mixture was quenched with 1 N aq. NaHCO$_3$ (50 mL) and extracted with DCM (3×50 mL). The organic layers were combined, dried (Na$_2$SO$_4$), and concentrated. Chromatography of the residue (SiO$_2$; 2-5% 2 M NH$_3$ in MeOH/DCM) gave the title compound (1.20 g, 74%).

B. (5-Hydroxymethyl-pyridin-2-yl)-(4-isopropyl-piperazin-1-yl)-methanone.

A solution of 6-(4-isopropyl-piperazine-1-carbonyl)-nicotinic acid methyl ester (0.500 g, 1.72 mmol) in THF (15 mL) was cooled to −78° C. in a dry ice bath. A solution of lithium tri-tert-butoxyaluminohydride (1 M in THF, 3.44 mL) was then added drop-wise to the reaction mixture. The resulting solution was allowed to come to rt and was stirred for 18 h. The reaction was quenched with satd. aq. potassium sodium tartrate (Rochelle's salt, 15 mL) and extracted with DCM (3×50 mL). The organic layers were combined, dried (Na$_2$SO$_4$), and concentrated to give the title compound (0.275 g, 61%).

Step C. 6-(4-Isopropyl-piperazine-1-carbonyl)-pyridine-3-carbaldehyde.

To a solution of (5-hydroxymethyl-pyridin-2-yl)-(4-isopropyl-piperazin-1-yl)-methanone (0.275 g, 1.10 mmol) in DCM (30 mL) was added MnO$_2$ (0.400 g., 5.20 mmol). The reaction was stirred for 6 h, filtered through a pad of diatomaceous earth, and concentrated to give the desired aldehyde (0.250 g, 95%).

Step D. (4-Isopropyl-piperazin-1-yl)-(5-piperidin-1-ylmethyl-pyridin-2-yl)-methanone.

To a solution of 6-(4-isopropyl-piperazine-1-carbonyl)-pyridine-3-carbaldehyde (0.250 g, 0.96 mmol) and piperidine (0.11 mL, 1.10 mmol) in DCM (20 mL) was added NaB(OAc)$_3$H (0.300 g, 1.44 mmol). After 18 h, 1 N NaOH (15 mL) was added and the mixture was extracted with DCM (3×25mL). The organic layers were combined, dried (Na$_2$SO$_4$), and concentrated. Chromatography of the resulting residue (SiO$_2$: 4-8% 2 M NH$_3$ in MeOH/DCM) gave the title compound as an oil (0.030 g, 9%). MS (ESI): exact mass calcd. for C$_{19}$H$_{30}$N$_4$O, 330.2; m/z found, 331.5 [M+H]$^+$. $^1$H NMR (400 MHz, CDCl$_3$): 8.49 (s, 1H), 7.77 (dd, J=7.8, 2.0, 1H), 7.58 (d, J=7.8, 1H), 3.82 (t, J=5.0, 2H), 3.61 (t, J=5.0, 2H), 3.49 (s, 2H), 2.75-2.72 (m, 1H), 2.62 (t, J=5.0, 2H), 2.51 (t, J=5.0, 2H), 2.37 (br s, 4H), 1.60-1.54 (m, 4H), 1.45-1.43 (m, 2H), 1.05 (d, J=6.6, 6H).

Example 4

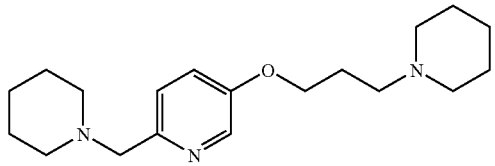

2-Piperdin-1-ylmethyl-5-(3-piperdin-1-yl-propoxy)-pyridine

Step A. (5-Hydroxy-pyridin-2-yl)-piperidin-1-yl-methanone.

To a solution of 5-hydroxy-2-pyridine carboxylic acid (2.00 g, 14.0 mmol) and piperidine (1.5 mL, 15 mmol) in DCM (150 mL) was added HOBt (2.80 g, 21.0 mmol), EDC (4.00 g, 21.0 mmol), and N-methyl morpholine (8.5 mL, 84 mmol). After 18 h the reaction mixture was concentrated.

Chromatography of the residue (SiO$_2$; 5-10% 2 M NH$_3$ in MeOH/DCM) gave the title compound as a solid (1.30 g, 43%).

Step B. 6-Piperidin-1-ylmethyl-pyridin-3-ol.

To a solution of (5-hydroxy-pyridin-2-yl)-piperidin-1-yl-methanone (1.30 g, 6.31 mmol) in THF (100 mL) was added borane-dimethylsulfide complex (1.75 mL, 18.9 mmol). After 18 h the solvent was removed and the residue was diluted with MeOH (50 mL) and heated to 60° C. After 2 h the solvent was evaporated and chromatography of the residue (SiO$_2$: 4-8% 2 M NH$_3$ in MeOH/DCM) gave the title compound as an oil (0.225 g, 17%).

Step C. 5-(3-Chloro-propoxy)-2-piperidin-1ylmethyl-pyridine.

A solution of 6-piperidin-1-ylmethyl-pyridin-3-ol (0.225 g, 1.17 mmol), 1-bromo-3-chloro propane (0.23 mL, 2.34 mmol), and K$_2$CO$_3$ (0.483 g, 3.50 mmol) in acetone (10 mL) was heated to reflux temperature. After 10 h the reaction mixture was cooled to rt, diluted with acetone (50 mL) and filtered through a pad of diatomaceous earth. The filtrate was concentrated, giving the crude title compound as an oil (0.250 g, 80%).

Step D. 2-Piperdin-1-ylmethyl-5-(3-piperdin-1-yl-propoxy)-pyridine.

A solution of 5-(3-chloro-propoxy)-2-piperidin-1ylmethyl-pyridine (0.25 g, 0.86 mmol), piperidine (0.09 mL, 0.94 mmol), KI (0.003 g, 0.017 mmol), and Na$_2$CO$_3$ (0.045 g, 0.43 mmol) in 1-butanol (5 mL) was heated to 95° C. After 18 h the reaction mixture was concentrated, diluted with DCM (50 mL) and filtered through a pad of diatomaceous earth. The filtrate was concentrated and chromatography of the residue (SiO$_2$: 3-8% 2 M NH$_3$ in MeOH/DCM) gave the title compound as an oil (0.025 g, 10%). MS (ESI): exact mass calcd. for C$_{19}$H$_{31}$N$_3$O, 317.3; m/z found, 318.5. $^1$H NMR (400 MHz, CDCl$_3$): 8.23 (d, J=2.8, 1H), 7.29 (d, J=8.1, 1H), 7.16 (dd, J=8.6, 3.0, 1H), 4.03 (t, J=6.3, 2H), 3.55 (s, 2H), 2.48-2.40 (m, 10H), 2.01-1.96 (m, 2H), 1.61-1.46 (m, 8H), 1.43 (br s, 4H).

Example 5

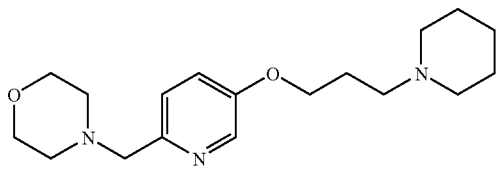

4-[5-(3-Piperidin-1-yl-propoxy)-pyridin-2-ylmethyl]-morpholine

This compound was prepared in a similar fashion as Example 4 substituting morpholine for piperidine in step A. MS (ESI): exact mass calcd. for C$_{18}$H$_{29}$N$_3$O$_2$, 319.2; m/z found, 320.5 [M+H]$^+$. $^1$H NMR (400 MHz, CDCl$_3$): 8.24 (d, J=2.5, 1H), 7.28 (d, J=8.6, 1H), 7.16 (dd, J=8.3, 2.8, 1H), 4.04 (t, J=6.3, 2H), 3.72 (t, J=4.7, 4H), 3.58 (s, 2H), 2.49-2.46 (m, 6H), 2.39 (br s, 4H), 2.01-1.96 (m, 2H), 1.61-1.55 (m, 4H), 1.45-1.43 (br s, 2H).

Example 6

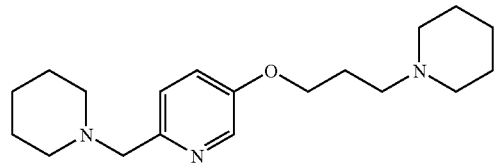

5-Piperidin-1-ylmethyl-2-(3-piperidin-1-yl-propoxy)-pyridine

Step A. (6-Bromo-Pyridin-3-yl)-piperidin-1-yl-methanone.

The intermediate is prepared in a similar fashion as described in Example 4, Step A, substituting 6-bromo-3-pyridine carboxylic acid for 5-hydroxy-2-pyridine carboxylic acid.

Step B. 2-Bromo-5-piperidin-1-ylmethyl-pyridine.

The intermediate is prepared in a similar fashion as described in Example 4, Step B, substituting (6-bromo-pyridin-3-yl)-piperidin-1-yl-methanone for (5-hydroxy-pyridin-2-yl)-piperidin-1-yl-methanone.

Step C. 5-Piperidin-1-ylmethyl-2-(3-piperidin-1-yl-propoxy)-pyridine.

To a suspension of NaH (1.5 mmol) in DMF is added 3-piperidin-1-yl-propan-1-ol (1.1 mmol). After 30 min, 2-bromo-5-piperidin-1-ylmethyl-pyridine (1 mmol) is added to the mixture. After 18 h, the reaction is extracted with ethyl acetate (100 mL) and washed with 1 N NaHCO$_3$ (50 mL) and H$_2$O(3×50 mL). The organic layer is dried, concentrated, and chromatographed on SiO$_2$ to provide the title compound.

Example 7

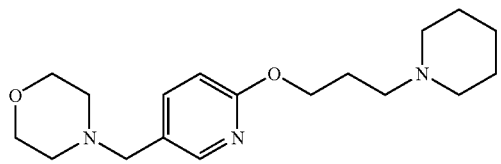

4-[6-(3-Piperidin-1-yl-propoxy)-pyridin-3-ylmethyl]-morpholine

This compound is synthesized in a similar fashion as Example 6 using morpholine instead of piperidine in step A.

Example 8

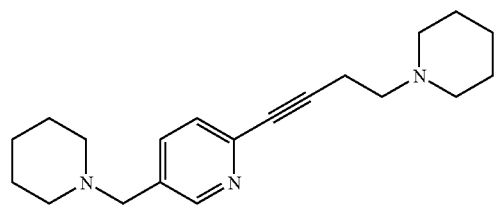

2-(4-Piperidin-1-yl-but-1-ynyl)-5-piperidin-1-ylmethyl-pyridine

Step A. Trifluoro-methanesulfonic acid 5-piperidin-1-ylmethyl-pyridin-2-yl ester.

A solution of 6-piperidin-1-ylmethyl-pyridin-3-ol (0.225 g, 1.17 mmol), N-phenyltriflouromethanesulfonamide (0.50 g, 1.41 mmol), and TEA (0.50 mL, 3.50 mmol) in DCM (20 mL) was heated at reflux for 18 h. The solvent was removed and chromatography of the residue (SiO$_2$: 0-3% 2 M NH$_3$ in MeOH/DCM) gave the title compound as a solid (0.036 g, 95%).

Step B. 2-(4-Piperidin-1-yl-but-1-ynyl)-5-piperidin-1-ylmethyl-pyridine.

To a solution of trifluoro-methanesulfonic acid 5-piperidin-1-ylmethyl-pyridin-2-yl ester (0.10 g, 0.31 mmol), 1-but-3-ynyl-piperidine (0.051 g, 0.37 mmol), and TEA (2 mL) in dry DMF (1 mL) was added dichlorobis(triphenylphosphine)-palladium(II) (0.004 g, 0.006 mmol) and copper(I) iodide (0.004 g, 0.016 mmol). The reaction mixture was heated at 80° C. for 4 h, cooled to rt, diluted with DCM (25 mL), and filtered through a pad of diatomaceous earth. The mixture was diluted with 1 N NaOH (25 mL) and extracted with DCM (3×25 mL). The organic layers were combined, dried (Na$_2$SO$_4$), and concentrated, and chromatography of the resulting residue (SiO$_2$: 3-6% 2 M NH$_3$ in MeOH/DCM) gave the title compound (0.01 g, 10%). MS (ESI): exact mass calcd. for C$_{20}$H$_{29}$N$_3$, 311.2; m/z found, 312.5 [M+H]$^+$. $^1$H NMR (400 MHz, CDCl$_3$): 8.45 (d, J=2.0, 1H), 7.62 (d, J=8.3, 1H), 7.25 (d, J=8.1, 1H), 3.47 (s, 2H), 2.74-2.70 (m, 4H), 2.62-2.59 (m, 4H), 2.37 (br s, 4H), 1.65-1.55 (m, 8H), 1.46-1.44 (m, 4H).

Example 9

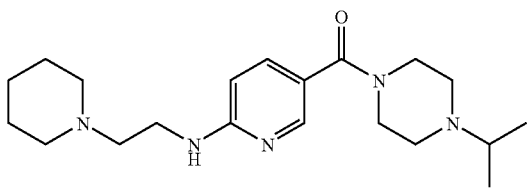

(4-Isopropyl-piperazin-1-yl)-[6-(2-piperidin-1-yl-ethylamino)-pyridin-3-yl]-methanone Step A. (6-Chloro-pyridin-3-yl)-(4-isopropyl-piperazin-1-yl)-methanone.

To a solution of 6-chloronicotinic acid (0.985 g, 6.25 mmol) and 1-isopropyl-piperazine (1.50 g, 7.50 mmol) in DCM (100 mL) was added HOBt (1.20 g, 9.40 mmol), EDC (1.80 g, 9.40 mmol), and N-methyl morpholine (3.4 mL, 31.3 mmol). After 18 h the reaction was diluted with 1 N NaOH (50 mL) and extracted with DCM (3×50 mL). The organic extracts were combined, dried (Na$_2$SO$_4$), and concentrated. Chromatography of the residue (SiO$_2$: 2-4% 2 M NH$_3$ in MeOH/DCM) gave the title compound as a solid (0.934 g, 56%).

Step B. (4-Isopropyl-piperazin-1-yl)-[6-(2-piperidin-1-yl-ethylamino)-pyridin-3-yl]-methanone.

A solution of (6-chloro-pyridin-3-yl)-(4-isopropyl-piperazin-1-yl)-methanone (0.20 g, 0.75 mmol) and 1-(2-aminoethyl)-piperidine (0.16 mL, 1.13 mmol) in 1-butanol (10 mL) was heated at reflux temperature. After 18 h the reaction was concentrated, treated with 1 N aq. NaHCO$_3$ (25 mL), and extracted with DCM (3×25 mL). The organic layers were combined, dried (Na$_2$SO$_4$), and concentrated. Chromatography of the residue (SiO$_2$: 2-5% 2 M NH$_3$ in MeOH/DCM) gave the title compound as an oil (0.050 g, 20%). MS (ESI): exact mass calcd. for C$_{20}$H$_{33}$N$_5$O, 359.3; m/z found, 360.2 [M+H]$^+$. $^1$H NMR (400 MHz, CDCl$_3$): 8.20 (d, J=1.8, 1H), 7.54 (dd, J=8.6, 2.3, 1H), 6.40 (d, J=9.0, 1H), 5.49 (br s, 1H), 3.65 (br s, 4H), 3.39-3.35 (m, 2H), 2.74-2.70 (m, 1H), 2.59-2.57 (m, 2H), 2.53 (br s, 4H), 2.42 (br s, 4H), 1.62-1.56 (m, 4H), 1.46-1.45 (m, 2H), 1.04 (d, 6.5, 6H).

Example 10

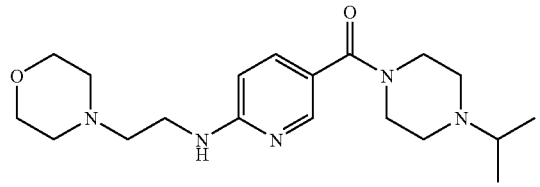

(4-Isopropyl-piperazin-1-yl)-[6-(2-morpholin-4-yl-ethylamino)-pyridin-3-yl]-methanone This compound was prepared in a similar fashion as Example 9 using 2-morpholin-4-yl-ethylamine in place of 1-(2-aminoethyl)-piperidine in step B. MS (ESI): exact mass calcd. for C$_{19}$H$_{31}$N$_5$O$_2$, 361.3; m/z found, 362.2 [M+H]$^+$. $^1$H NMR (400 MHz, CDCl$_3$): 8.20 (d, J=1.9, 1H), 7.55 (dd, J=8.6, 2.3, 1H), 6.40 (d, J=9.0, 1H), 5.36 (br s, 1H), 3.73-3.71 (m, 4H), 3.66-3.62 (m, 4H), 3.41-3.37 (m, 2H), 2.73-2.70 (m, 1H), 2.64-2.60 (m, 2H), 2.52-2.47 (m, 8H), 1.04 (d, J=6.5, 6H).

Example 11

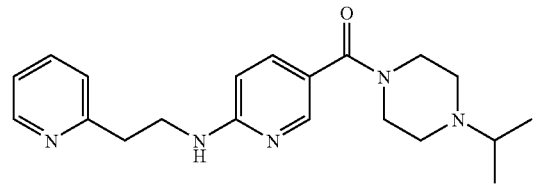

(4-Isopropyl-piperazin-1-yl)-[6-(2-pyridin-2-yl-ethylamino)-pyridin-3-yl]-methanone This compound was prepared in a similar fashion as Example 9 using 2-pyridin-2-yl-ethylamine in place of 1-(2-aminoethyl)-piperidine in step B. MS (ESI): exact mass calcd. for C$_{20}$H$_{27}$N$_5$O, 353.46; m/z found, 354.2 [M+H]$^+$. $^1$H NMR (400 MHz, CDCl$_3$): 8.57-8.54 (m, 1H), 8.20 (s, 1H), 7.63-7.59 (m, 1H), 7.53 (dd, J=8.6, 2.3, 1H), 7.18-7.14 (m, 2H), 6.39 (d, J=9.2, 1H), 5.43 (br s, 1H), 3.78-3.73 (m, 2H), 3.65 (br s, 4H), 3.10 (t, J =6.5, 2H), 2.74-2.70 (m, 1H), 2.52 (br s, 4H), 1.05 (d, 6.4, 6H).

Example 12

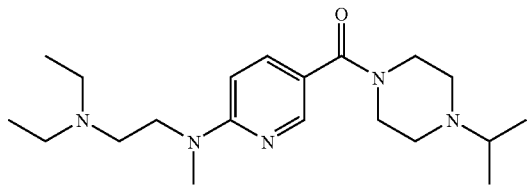

{6-[(2-Diethylamino-ethyl)-methyl-amino]-pyridin-3-yl}-(4-isopropyl-piperazin-1-yl)-methanone This compound was prepared in a similar fashion as Example 9 using N,N-diethyl-N'-methyl-ethane-1,2-diamine in place of 1-(2-aminoethyl)-piperidine in step B. MS (ESI): exact mass calcd. for $C_{20}H_{35}N_5O$, 361.2; m/z found, 362.2 [M+H]$^+$. $^1$H NMR (400 MHz, CDCl$_3$): 8.26 (s, 1H), 7.58 (dd, J=8.8, 2.3, 1H), 6.47 (d, J=9.3, 1H), 3.66-3.63 (m, 6H), 3.10 (s, 3H), 2.74-2.71 (m, 1H), 2.64-2.52 (m, 10H), 1.06-1.01 (m, 12H).

Example 13

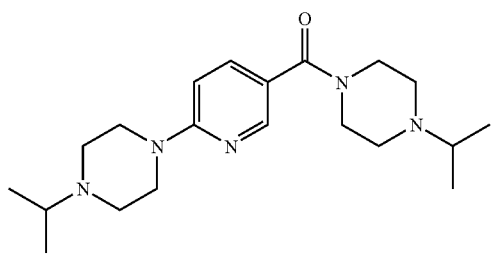

(4-Isopropyl-piperazin-1-yl)-[6-(4-isopropyl-piperazin-1-yl)-pyridin-3-yl]-methanone This compound was prepared in a similar fashion as Example 9 using 1-isopropyl-piperazine in place of 1-(2-aminoethyl)-piperidine in step B. MS (ESI): exact mass calcd. for $C_{20}H_{33}N_5O$, 359.5; m/z found, 360.2 [M+H]$^+$. $^1$H NMR (400 MHz, CDCl$_3$): 8.27(s, 1H), 7.60 (dd, J=8.8, 2.3, 1H), 6.62 (d, J=8.8, 1H), 3.63-3.60 (m, 8H), 2.74-2.70 (m, 2H), 2.62-2.60 (m, 4H), 2.53 (br s, 4H), 1.07-1.04 (m, 12H).

Example 14

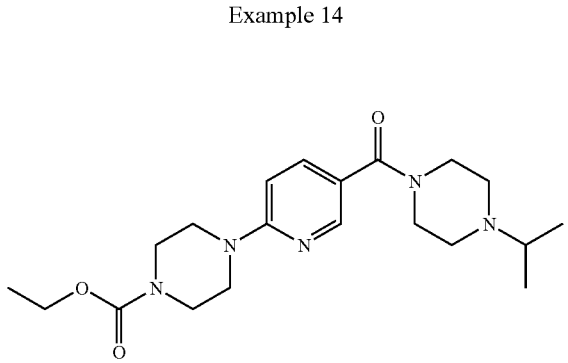

4-[5-(4-Isopropyl-piperazine-1-carbonyl)-pyridin-2-yl]-piperazine-1-carboxylic acid ethyl ester This compound was prepared in a similar fashion as Example 9 using piperazine-1-carboxylic acid ethyl ester in place of 1-(2-aminoethyl)-piperidine in step B. MS (ESI): exact mass calcd. for $C_{20}H_{31}N_5O_3$, 389.2; m/z found, 390.2 [M+H]$^+$. $^1$H NMR (400 MHz, CDCl$_3$): 8.28 (s, 1H), 7.60 (dd, J=8.8, 2.3, 1H), 6.62 (d, J=8.8, 1H), 4.20-4.16 (m, 2H), 3.63-3.60 (m, 10H), 2.73 (br s, 1H), 2.54 (br s, 4H), 1.60 (br s, 2H), 1.31-1.28 (m, 3H), 1.06 (d, 6.5, 6H).

Example 15

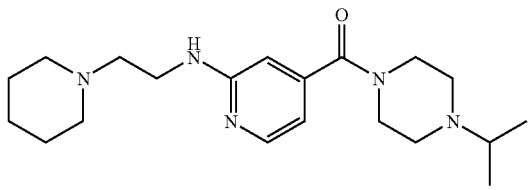

(4-Isopropyl-piperazin-1-yl)-[6-(4-methyl-piperazin-1-yl)-pyridin-3-yl]-methanone This compound was prepared in a similar fashion as Example 9 using 1-methyl-piperazine in place of 1-(2-aminoethyl)-piperidine in step B. MS (ESI): exact mass calcd. for $C_{18}H_{29}N_5O$, 331.2; m/z found, 332.2 [M+H]$^+$. $^1$H NMR (400 MHz, CDCl$_3$): 8.28 (s, 1H), 7.60 (dd, J=8.8, 2.3, 1H), 6.62 (d, J=8.8, 1H), 3.63-3.60 (m, 8H), 2.74-2.70 (m, 1H), 2.52-2.48 (m, 8H), 2.35 (s, 3H) 1.05 (d, J=6.5, 6H).

Example 16

(4-Isopropyl-piperazin-1-yl)-[2-(2-piperidin-1-yl-ethylamino)-pyridin-4-yl]-methanone Step A. (2-Chloro-pyridin-4-yl)-(4-isopropyl-piperazin-1-yl)-methanone.

The title compound was prepared in a manner similar to that described in Step A of Example 9 using 2-chloro-isonicotinic acid and 1-isopropyl-piperazine.

Step B. (4-Isopropyl-piperazin-1-yl)-[2-(2-piperidin-1-yl-ethylamino)-pyridin-4-yl]-methanone.

This compound was prepared in a similar fashion as step B in Example 9 using (2-chloro-pyridin-4-yl)-piperidin-1-yl-methanone and 2-piperidin-1-yl-ethylamine. MS (ESI): exact mass calcd. for $C_{20}H_{33}N_5O$, 359.3; m/z found, 360.1 [M+H]$^+$. $^1$H NMR (400 MHz, CDCl$_3$): 8.11 (d, J=5.1, 1H), 6.48 (dd, J=5.1, 1.3, 1H), 6.37 (s, 1H), 5.34 (br s, 1H), 3.75 (br s, 2H), 3.40-3.32 (m, 4H), 2.73-2.71 (m, 1H), 2.59-2.54 (m, 4H), 2.45-2.40 (m, 6H) 1.59-1.55 (m, 4H), 1.45-1.44 (m, 2H), 1.05 (d, J=6.5, 6H).

Example 17

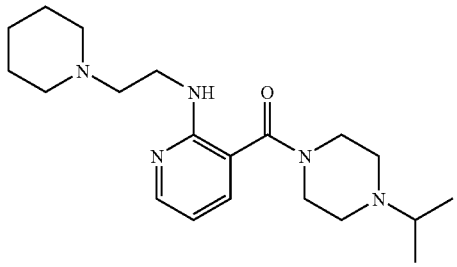

(4-Isopropyl-piperazin-1-yl)-[2-(2-piperidin-1-yl-ethylamino)-pyridin-3-yl]-methanone Step A. (2-Chloro-pyridin-3-yl)-(4-isopropyl-piperazin-1-yl)-methanone.

The title compound was prepared in a manner similar to that described in Step A of Example 9 using 2-chloro-nicotinic acid and 1-isopropyl-piperazine.

Step B. (4-Isopropyl-piperazin-1-yl)-[2-(2-piperidin-1-yl-ethylamino)-pyridin-3-yl]-methanone.

This compound was prepared in a similar fashion as step B Example 9 using (2-chloro-pyridin-3-yl)-piperidin-1-yl-methanone and 2-piperidin-1-yl-ethylamine. MS: exact mass calcd. for $C_{20}H_{33}N_5O$, 359.3; m/z found, 360.3 [M+H]$^+$. $^1$H NMR (400 MHz, CDCl$_3$): 8.11 (d, J=5.1, 1H), 6.48 (dd, J=5.1, 1.3, 1H), 6.37 (s, 1H), 5.34 (brs, 1H), 3.75 (brs, 2H), 3.40-3.32 (m, 4H), 2.73-2.71 (m, 1H), 2.59-2.54 (m, 4H), 2.45-2.40 (m, 6H), 1.59-1.55 (m, 4H), 1.45-1.44 (m, 2H), 1.05 (d, J=6.5, 6H).

Example 18

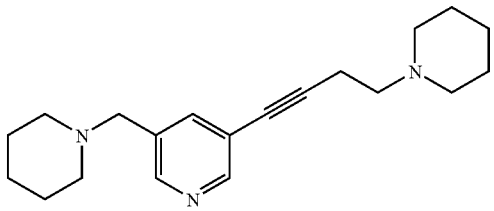

3-(4-Piperidin-1-yl-but-1-ynyl)-5-piperidin-1-ylmethyl-pyridine

Step A. (5-Bromo-pyridin-3-yl)-methanol.

To a solution of 5-bromonicotinic acid (20.00 g, 97.00 mmol) in anhydrous THF (250 mL) was added a solution of BH$_3$ (1 M in THF, 197 mL) slowly at rt over a period of 1 h. The reaction mixture was stirred for 1 h at rt and then was heated at reflux temperature for 5 h. The reaction mixture was cooled to rt and treated with 1 M HCl (100 mL) drop-wise. The resulting mixture was stirred for 1 h and treated with 10% aq. NaOH until pH 10. The solution was then extracted with ethyl acetate (4×200 mL). The combined organic extracts were washed with H$_2$O, dried over anhydrous Na$_2$SO$_4$, filtered and concentrated to yield the crude alcohol (10.71 g). Purification of the crude compound (SiO$_2$: 0-5% 2 M NH$_3$ in MeOH/DCM) gave (5-bromo-pyridin-3-yl)-methanol (4.14 g, 22%).

Step B. 5-Bromo-pyridine-3-carbaldehyde.

(5-Bromo-pyridin-3-yl)-methanol (1.13 g, 6.00 mmol) was dissolved in CHCl$_3$ (40 mL) and treated with MnO$_2$ (3.60 g). The reaction mixture was heated at reflux temperature for 3 h. The hot reaction mixture was filtered through a pad of diatomaceous earth and the filtrate was concentrated to yield the title compound (0.570 g, 51%).

Step C. 3-Bromo-5-piperidin-1-yimethyl-pyridine.

5-Bromo-pyridine-3-carbaldehyde (0.190g, 1 mmol), NaB(OAc)$_3$H (0.320 g, 1.50 mmol) and piperidine (0.090 g, 1.05 mmol) were suspended in DCM (8 mL) and the reaction mixture was stirred overnight at rt. The reaction was quenched by the addition of 1 M NaOH solution (5 mL) and the mixture was stirred for 1 h. The reaction mixture was extracted with DCM (3×15 mL). The organic extracts were combined, dried over Na$_2$SO$_4$, filtered, and concentrated to yield a crude oily product (0.18 g, 71%). This crude product was carried to the next step.

Step D. 3-(4-Piperidin-1-yl-but-1-ynyl)-5-piperidin-1-ylmethyl-pyridine. 3-Bromo-5-piperidin-1-ylmethyl-pyridine (0.353 g, 1.38 mmol), 1-but-3-ynyl-piperidine (0.380 g, 2.77 mmol), dichlorobis(triphenylphosphine)palladium(II) (0.097 g, 0.14 mmol), copper(I) iodide (0.027 g, 0.14 mmol), and Ph$_3$P (0.131 g, 0.50 mmol) were added to a mixture of DMF (0.50 mL) and Et$_2$N (3.00 mL) under nitrogen. The system was degassed with vacuum and filled with nitrogen three times, then heated at 120-125° C. for 2 h. The reaction mixture was cooled and treated with satd. aq. NaHCO$_3$ (15 mL) and stirred for 30 min. The reaction mixture was extracted with DCM (3×30 mL) and the combined organic phases washed with H$_2$O (2×20 mL), dried over anhydrous Na$_2$SO$_4$, filtered and concentrated. The residue was purified (SiO$_2$: 0-7% 2 M NH$_3$ in MeOH/DCM) to yield the title compound (0.018 g, 8%). MS (ESI): exact mass calcd. for $C_{20}H_{29}N_3$, 311.46; m/z found 312.5 [M+H]$^+$. $^1$H NMR (500 MHz, CDCl$_3$): 8.48 (d, J=1.9, 1H), 8.39 (d, J=1.6, 1H), 7.66-7.64 (m, 1H), 3.42 (s, 2H), 2.69-2.59 (m, 4H), 2.51-2.41 (m, 4H), 2.40-2.30 (m, 4H), 1.64-1.51(m, 8H), 1.48-1.37 (m, 4H).

Example 19

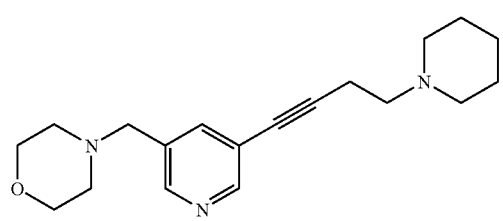

4-[5-(4-Piperidin-1-yl-but-1-ynyl)-pyridin-3-ylmethyl]-morpholine

Step A. 4-(5-Bromo-pyridin-3-ylmethyl)-morpholine.

The title compound was prepared in a similar way as described in Example 18, Step C, using 5-bromo-pyridine-3-carbaldehyde and morpholine. The crude compound was purified (SiO$_2$: 0-3% 2 M NH$_3$ in MeOH/DCM) to provide the title compound (61%).

Step B. 4-[5-(4-Piperidin-1-yl-but-1-ynyl)-pyridin-3-ylmethyl]-morpholine.

This compound was made in a similar way as described in Example 18, Step D, using 4-(5-bromo-pyridin-3-ylmethyl)-morpholine and 1-but-3-ynyl-piperidine (57%). MS (ESI): exact mass calcd. for C$_{19}$H$_{27}$N$_3$O, 313.45; m/z found, 314.5 [M+H]$^+$. $^1$H NMR (500 MHz, CDCl$_3$): 8.49 (d, J=1.9,1H), 8.40 (d, J=1.6,1H), 7.66-7.64 (m, 1H), 3.68 (t, J=4.5, 4H), 3.45 (s, 2H), 2.67-2.58 (m, 4H), 2.49-2.38 (m, 8H), 1.62-1.52 (m, 4H), 1.46-1.40 (m, 2H).

Example 20

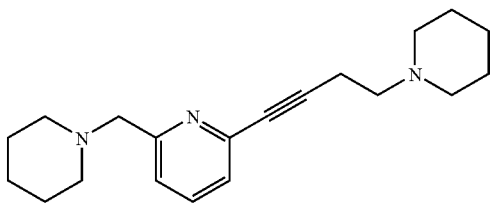

2-(4-Piperidin-1-yl-but-1-ynyl)-6-piperidin-1-ylmethyl-pyridine

Step A. 6-Bromo-pyridine-2-carbaldehyde.

To a –10° C. solution of n-BuLi (2.5 M in hexane, 5.6 mL, 14 mmol) in anhydrous toluene (20 mL) was added a solution of n-BuMgCl (2 M in THF, 3.5 mL) over 20 min, maintaining the temperature between –10° C. and 0° C. The mixture was stirred at –10° C. for 30 min. A solution of 2,6-dibromopyridine (4.74 g, 20 mmol) in toluene (20 mL) was added drop-wise over a period of 30 min while keeping the temperature below –5° C. The resulting suspension was stirred at –10° C. for 2.5 h. The mixture was transferred via cannula to a –10° C. solution of DMF (1.9 g, 26 mmol) in toluene (10 mL). The solution was allowed to stand between –5° C. and –10° C. for 30 min and then was transferred into a solution of citric acid (8.00 g) in H$_2$O (15 mL), maintaining the temperature below 20° C. The resulting solution was stirred for 10 min and the layers were separated. The organic layer was dried over Na$_2$SO$_4$, filtered, and concentrated. The residue was purified (SiO$_2$: 10% ethyl acetate/hexanes) to afford the title compound (1.94 g, 52%).

Step B. 2-Bromo-6-piperidin-1-yimethyl-pyridine.

The title compound was prepared in a manner similar to that described in Example 18, Step C, using 6-bromo-pyridine-2-carbaldehyde (0.406 g, 2.18 mmol) and piperidine (0.186 g, 2.18 mmol). The crude product was purified (SiO$_2$: 0-4% 2 M NH$_3$ in MeOH/DCM) to provide the title compound (0.46 g, 83%).

Step C. 2-(4-Piperidin-1-yl-but-1-ynyl)-6-piperidin-1-ylmethyl-pyridine.

The title compound was prepared in a manner similar to that described in Example 18, Step D, using 2-bromo-6-piperidin-1-ylmethyl-pyridine and 1-but-3-ynyl-piperidine (56%). MS (ESI): exact mass calcd. for C$_{20}$H$_{29}$N$_3$, 311.46; m/z found, 312.5 [M+H]$^+$. $^1$H NMR (500 MHz, CDCl$_3$): 7.54 (t, J=7.7, 1H), 7.38 (d, J=7.7, 1H), 7.20 (d, J=7.4, 1H), 3.58 (s, 2H), 2.67-2.57 (m, 4H), 2.46-2.34 (m, 8H), 1.60-1.50 (m, 8H), 1.44-1.36 (m, 4H).

Example 21

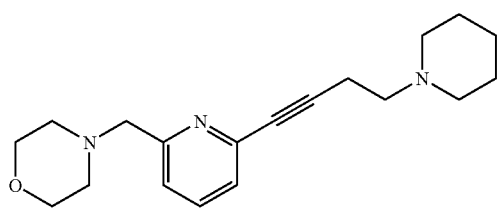

4-[6-(4-Piperidin-1-yl-but-1-ynyl)-pyridin-2-ylmethyl]-morpholine

Step A. 4-(6-Bromo-pyridin-2-ylmethyl)-morpholine.

The title compound was prepared in a manner similar to that described in Example 18, Step C, using 6-bromo-pyridine-2-carbaldehyde (0.415 g, 2.23 mmol) and morpholine (0.195 g, 2.23 mmol). The crude product was purified (SiO$_2$: 0-3% 2 M NH$_3$ in MeOH/DCM) to give the title compound (0.352 g, 61%).

Step B. 4-[6-(4-Piperidin-1-yl-but-1-ynyl)-pyridin-2-ylmethyl]-morpholine.

The title compound (19%) was prepared in a manner similar to that described in Example 18, Step D, using 4-(6-bromo-pyridin-2-ylmethyl)-morpholine (0.278 g, 1.08 mmol) and 1-but-3-ynyl-piperidine (0.297 g, 2.16 mmol). MS (ESI): exact mass calcd. for C$_{19}$H$_{27}$N$_3$O, 313.45; m/z found, 314.4 [M+H]$^+$. $^1$H NMR (500 MHz, CDCl$_3$): 7.52 (t, J=7.8, 1H), 7.32 (dd, J=8.0, 1.1, 1H), 7.20 (dd, J=7.1, 1.1, 1H), 3.65 (t, J=4.6, 4H), 3.58 (s, 2H), 2.65-2.55 (m, 4H), 2.46-2.37 (m, 8H), 1.57-1.49 (m, 4H), 1.41-1.34 (m, 2H).

Example 22

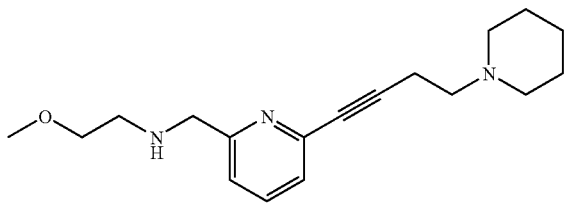

(2-Methoxy-ethyl)-[6-(4-piperidin-1-yl-but-1-ynyl)-pyridin-2-ylmethyl]-amine

Step A. (6-Bromo-pyridin-2-ylmethyl)-(2-methoxy-ethyl)-amine.

The title compound was prepared in a manner similar to that described in Example 18, Step C, using 6-bromo-pyridine-2-carbaldehyde (0.275 g, 1.48 mmol) and 2-methoxy-ethylamine (0.111 g, 1.48 mmol). The crude product was purified (SiO$_2$: 0-5% MeOH/DCM) to yield the title compound (0.34 g, 94%).

Step B. (2-Methoxy-ethyl)-[6-(4-piperidin-1-yl-but-1-ynyl)-pyridin-2-ylmethyl]-amine.

The title compound (13%) was prepared in a manner similar to that described in Example 18, Step D, using (6-bromo-pyridin-2-ylmethyl)-(2-methoxy-ethyl)-amine (0.300 g, 1.23 mmol) and 1-but-3-ynyl-piperidine (0.336 g, 2.45 mmol). MS (ESI): exact mass calcd. for $C_{18}H_{27}N_3O$, 301.44; m/z found, 302.4 [M+H]$^+$. $^1$H NMR (500 MHz, CDCl$_3$): 7.56 (t, 7.7, 1H), 7.26 (d, J=7.1, 1H), 7.23 (d, J=7.7, 1H), 3.90 (s, 2H), 3.52-3.45 (m, 2H), 3.34 (s, 3H), 2.80 J=5.2, 2H), 2.70-2.59 (m, 4H), 2.48-2.40 (m, 4H), 1.67-1.54 (m, 5H), 1.46-1.38 (m, 2H).

Example 23

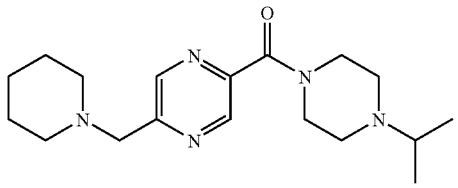

(4-Isopropyl-piperazin-1-yl)-(5-piperidin-1-ylmethyl-pyrazin-2-yl)-methanone

Step A. 5-Dibromomethyl-pyrazine-2-carboxylic acid methyl ester.

5-Methyl-pyrazine-2-carboxylic acid methyl ester (1.60 g, 10.5 mmol; Macdonald, S. J. F. et al. J.Med.Chem. 2002, 45(18):3878-3890.), N-bromosuccinimide (5.62 g, 31.6 mmol), and dibenzoyl peroxide (0.255 g, 1.05 mmol) were dissolved in CCl$_4$ (80 mL). The mixture was heated at reflux for 18 h. The reaction mixture was cooled and washed with 10% aq. Na$_2$SO$_3$ (2×20 mL) and H$_2$O (1×30 mL). The organic phase was dried over Na$_2$SO$_4$, filtered, and concentrated to yield a brown oily crude material (2.41 g). The crude product was purified (SiO$_2$: 0-20% ethyl acetate/hexanes) to give the title compound (1.00 g, 31%).

Step B. 5-Formyl-pyrazine-2-carboxylic acid methyl ester.

A solution of 5-dibromomethyl-pyrazine-2-carboxylic acid methyl ester (1.00 g, 3.23 mmol) in a mixture of ethanol (20 mL) and THF (10 mL) was heated to 80° C. A solution of silver nitrate (2.20 g, 12.9 mmol) in H$_2$O (4 mL) was added. The reaction mixture was heated at 80° C. for 1.25 h and was filtered while hot. The filtrate was concentrated to yield the title compound (1.36 g). This material was carried to the next step without purification.

Step C. 5-Piperidin-1-ylmethyl-pyrazine-2-carboxylic acid methyl ester.

A mixture of 5-formyl-pyrazine-2-carboxylic acid methyl ester (0.400 g, 2.40 mmol), piperidine (0.204 g, 2.40 mmol), and NaB(OAc)$_3$H (1.40 g, 3.60 mmol) in DCM (10 mL) was stirred for 18 h at rt. The reaction was quenched by the addition of 10% aq. NaOH (10 mL) and the mixture was stirred for 30 min. The mixture was extracted with DCM (3×20 mL). The combined organic extracts were dried over Na$_2$SO$_4$, filtered, and concentrated to yield the title compound (0.130 g, 23%).

Step D. 5-Piperidin-1-ylmethyl-pyrazine-2-carboxylic acid.

A mixture of 5-piperidin-1-ylmethyl-pyrazine-2-carboxylic acid methyl ester (0.125 g, 0.53 mmol) in dioxane (3 mL) was treated with 1 M aq. LiOH (0.53 mL, 0.53 mmol) and stirred for 18 h. The mixture was concentrated to yield the crude lithium salt of the acid (0.120 g).

Step E. (4-Isopropyl-piperazin-1-yl)-(5-piperidin-1-yimethyl-pyrazin-2-yl)-methanone.

A mixture of 5-piperidin-1-ylmethyl-pyrazine-2-carboxylic acid (0.125 g, 0.53 mmol), 1-isopropyl-piperazine dihydrochloride (0.117 g, 0.58 mmol), HOBt (0.086 g, 0.64 mmol) and N-methylmorpholine (0.323 g, 3.19 mmol) in DCM (7 mL) was stirred for 1 h. The mixture was then treated with EDC (0.122 g, 0.64 mmol) and stirring was continued for 18 h. The reaction was quenched by the addition of 1 N NaOH (10 mL), and was stirred for 30 min. The mixture was diluted with H$_2$O (10 mL) and extracted with DCM (3×15 mL). The combined organic layers were dried over Na$_2$SO$_4$, filtered, and concentrated to yield the crude product (0.145 g). The crude was purified on SiO$_2$ using 0-5% 2 M NH$_3$ in MeOH/DCM to provide the title compound (0.05 g, 26%). MS (ESI): exact mass calcd. for $C_{18}H_{29}N_5O$, 331.46; m/z found 332.5 [M+H]$^+$. $^1$HNMR (500 MHz, CDCl$_3$): 8.85 (d, J=1.4,1H), 8.64 (d, J=1.4, 1H), 3.82 (t, J=4.9, 2H), 3.68 (s, 2H), 3.63 (t, J=4.9, 2H), 2.77-2.70 (m, 1H), 2.62 (t, J=4.9, 2H), 2.53 (t, J=4.9, 2H), 2.48-2.42 (m, 4H), 1.63-1.57 (m, 4H), 1.49-1.42 (m, 2H), 1.05 (d, J=6.6, 6H).

Example 24

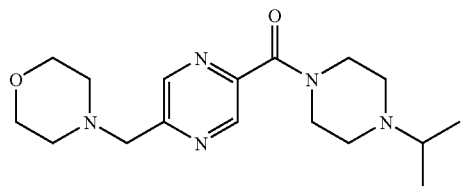

(4-Isopropyl-piperazin-1-yl)-(5-morpholin-4-ylmethyl-pyrazin-2-yl)-methanone

Step A. 5-Morpholin-4-yimethyl-pyrazine-2-carboxylic acid methyl ester.

The title compound was prepared in a manner similar to that described in Example 23, Step C, using 5-formyl-pyrazine-2-carboxylic acid methyl ester (0.78 g, 4.7 mmol) and morpholine (0.44 g, 5.2 mmol).

Step B. 5-Morpholin-4-ylmethyl-pyrazine-2-carboxylic acid.

Hydrolysis of 5-morpholin-4-ylmethyl-pyrazine-2-carboxylic acid methyl ester (0.28 g) was performed in a similar manner to that described in Example 23, Step D, to give the crude lithium salt of the acid (0.224 g).

Step C. (4-Isopropyl-piperazin-1-yl)-(5-morpholin-4-ylmethyl-pyrazin-2-yl)-methanone.

The title compound (0.022 g, 7%) was prepared in a manner similar to that described in Example 23, Step E. MS (ESI): exact mass calcd. for $C_{17}H_{27}N_5O$, 333.44; m/z found 334.5 [M+H]$^+$. $^1$H NMR (500 MHz, CDCl$_3$):8.87 (d, J=1.4, 1H), 8.64 (d, J=1.4, 1H), 3.84-3.79 (m, 2H), 3.76-3.71 (m, 6H), 3.63-3.59 (m, 2H), 2.77-2.71 (m, 1H), 2.64-2.60 (m, 2H), 2.55-2.44 (m, 6 H), 1.05 (d, J=6.6, 6H).

Example 25

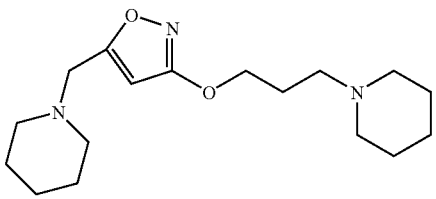

4-[3-(3-Piperidin-1-yl-propoxy)-isoxazol-5-ylmethyl]-piperidine

Step A. 3-(3-Piperidin-1-yl-propoxy)-isoxazole-5-carboxylic acid methyl ester.

3-Hydroxy-isoxazole-5-carboxylic acid methyl ester (0.859 g., 6.00 mmol) and 3-piperidin-1-yl-propan-1-ol (0.860 g., 6.00 mmol) were dissolved in DCM (30 mL), and polymer-supported Ph$_3$P resin (3 mmol/g, 3.1 g, 9.30 mmol) was added. The mixture was stirred for 10 min and di-tert-butyl azodicarboxylate (2.14 g, 9.30 mmol) was then added. The reaction mixture was stirred under nitrogen for 18 h. The reaction was quenched with 1 N NaOH (20 mL) and was stirred for 30 min. The resulting mixture was extracted with DCM (3×30 mL). The combined organic extracts were dried over Na$_2$SO$_4$, filtered, and concentrated to yield a crude oily product (3.1 g), which was purified (SiO$_2$: 5% 2 M NH$_3$ in MeOH/DCM) to yield the title compound (0.88 g, 58%). MS (ESI): exact mass calcd. for $C_{13}H_{20}N_2O_4$, 268.14; m/z found, 269.4 [M+H]$^+$. $^1$H NMR (500 MHz, CDCl$_3$): 6.53 (s, 1H), 4.34-4.30 (m, 2H), 3.94 (s, 3H), 2.47-2.34 ( 6H), 2.02-1.94 (m, 2H), 1.61-1.54 (m, 4H), 1.47-1.39 (m, 2H).

Step B. [3-(3-Piperidin-1-yl-propoxy)-isoxazol-5-yl]-methanol.

To a solution of 3-(3-piperidin-1-yl-propoxy)-isoxazole-5-carboxylic acid methyl ester (0.200 g, 0.750 mmol) in EtOH (15 mL) was added NaBH$_4$ (0.358 g, 11.2 mmol) was slowly over 30 min. The reaction mixture was heated at reflux overnight, then was cooled to rt and quenched by the addition of 1 N NaOH (10 mL). The mixture was stirred for 1 h, and then was extracted with DCM (3×30 mL). The combined organic extracts were dried over Na$_2$SO$_4$, filtered, and concentrated to yield the desired alcohol (0.177 g, 99%). MS (ESI): exact mass calcd. for $C_{12}H_{20}N_2O_3$, 240.15; m/z found, 241.3 [M+H]$^+$.

Step C. 1-[3-(5-Chloromethyl-isoxazol-3-yloxy)-propyl]-piperidine.

A mixture of [3-(3-piperidin-1-yl-propoxy)-isoxazol-5-yl]-methanol (0.150 g, 0.625 mmol) and neat thionyl chloride (4 mL) was heated at reflux for 3 h. The reaction mixture was cooled to rt and concentrated to give the desired chloride, which was carried to the next step without further purification.

Step D. 4-[3-(3-Piperidin-1-yl-propoxy)-isoxazol-5-ylmethyl]-piperidine.

1-[3-(5-Chloromethyl-isoxazol-3-yloxy)-propyl]-piperidine (0.15 g, 0.80 mmol) was dissolved in DCM (5 mL) and piperidine (0.24 mL, 2.4 mmol) was added slowly. The reaction mixture was stirred overnight at rt and then was concentrated to yield the crude product (0.140 g). The crude product was purified (SiO$_2$: 0-5% 2 M NH$_3$ in MeOH/DCM) to give the final product (0.118 g, 47.6%). MS (ESI): exact mass calcd. for $C_{17}H_{29}N_3O_2$, 307.23; m/z found 308.4 [M+H]$^+$. $^1$H NMR (500 MHz, CDCl$_3$): 5.75 (s, 1H), 4.25-4.20 (m, 2H), 3.53 (s, 2H), 2.47-2.31 (m, 10H), 1.98-1.90 (m, 2H), 1.61-1.52 (m, 8H), 1.45-1.35 (m, 4H).

Example 26

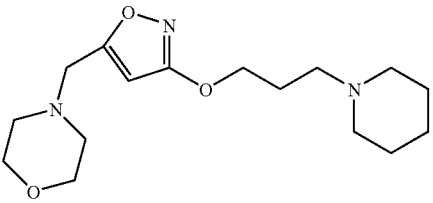

4-[3-(3-Piperidin-1-yl-propoxy)-isoxazol-5-ylmethyl]-morpholine

The title compound was prepared in a manner similar to that described in Example 25, Step D. MS (ESI): exact mass calcd. for $C_{16}H_{27}N_3O_3$, 309.21; m/z found, 310.5 [M+H]$^+$. $^1$H NMR (500 MHz, CDCl$_3$): 5.80 (s, 1H), 4.27-4.21 (m, 2H), 3.70 (t, J=4.7, 4H), 3.54 (s, 2H), 2.53-2.32 (m, 10H), 2.00-1.92 (m, 2H), 1.61-1.54 (m, 4H), 1.46-1.38 (m, 2H).

Example 27

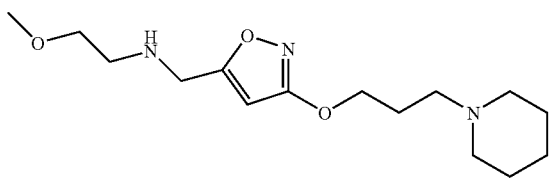

(2-Methoxy-ethyl)-[3-(3-piperidin-1-yl-propoxy)-isoxazol-5-ylmethyl]-amine

The title compound was prepared in a manner similar to that described in Example 25, Step D. MS (ESI): exact mass calcd. for $C_{15}H_{27}N_3O_3$, 297.21; m/z found, 298.5 [M+H]$^+$. $^1$H NMR (500 MHz, CDCl$_3$): 5.78 (s, 1H), 4.26-4.22 (m, 2H), 3.81 (br s, 2H), 3.50-3.46 (m, 2H), 3.35 (s, 3H), 2.82-2.79 (m, 2H), 2.45-2.40 (m, 2H), 2.40-2.33 (m, 3H), 1.99-1.92 (m, 2H), 1.87-1.76 (m, 2H), 1.60-1.54 (m, 4H), 1.46-1.39 (m, 2H).

Example 28

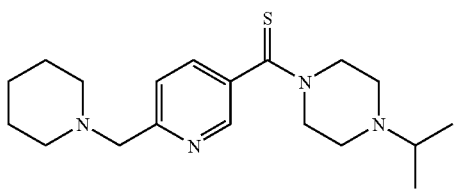

(4-Isopropyl-piperazin-1-yl)-(6-piperidin-1-ylmethyl-pyridin-3-yl)-methanethione A solution of (4-isopropyl-piperazin-1-yl)-(6-piperidin-1-ylmethyl-pyridin-3-yl)-methanone (Example 1, 80 mg, 0.24 mmol) and Lawesson's reagent (210 mg, 0.50 mmol) in THF was heated at reflux for 48 h. The reaction was cooled to rt and the solvent was removed in vacuo. Chromatography of the residue ($SiO_2$: 1-6% 2 M $NH_3$ in MeOH/DCM) gave the title compound as an oil. MS (ESI): exact mass calcd. for $C_{19}H_{30}N_4S$, 346.22; m/z found, 347.5 $[M+H]^+$.

Biology Example

A. Transfection of Cells with Human Histamine Receptor

Cells were grown to about 70% to 80% confluence and removed from the plate with trypsin and pelleted in a clinical centrifuge. The pellet was then re-suspended in 400 μL of complete media and transferred to an electroporation cuvette with a 0.4 cm gap between the electrodes (Bio-Rad #165-2088). One μg supercoiled $H_3$ receptor cDNA was added to the cells and mixed gently. The voltage for the electroporation was set at 0.25 kV and the capacitance was set at 960 μF. After electroporation the cells were diluted with 10 mL of complete media and were plated onto four 10 cm dishes at the following ratios: 1:20, 1:10, 1:5, and 1:2. The cells were allowed to recover for 24 h before adding 600 μg G-418. Colonies that survived selection were grown and tested. SK-N-MC cells were used because they give efficient coupling for inhibition of adenylate cyclase. The clones that gave the most robust inhibition of adenylate cyclase in response to histamine were used for further study.

B. $[^3H]$-N-Methylhistamine Binding

Cell pellets from histamine $H_3$ receptor-expressing SK-N-MC cells were homogenized in 50 mM TrisHCl/0.5 mM EDTA. Supernatants from an 800 g spin were collected and were recentrifuged at 30,000 g for 30 min. Pellets were re-homogenized in 50 mM Tris/5 mM EDTA (pH 7.4). Membranes were incubated with 0.8 nM $[^3H]$-N-methylhistamine plus/minus test compounds for 60 min at 25° C. and were harvested by rapid filtration over GF/C glass fiber filters (pre-treated with 0.3% polyethylenimine) followed by four washes with buffer. Filters were added to 5 mL of scintillation cocktail, and the signal was then counted on a liquid scintillation counter. Non-specific binding was defined with 10 μM histamine. $pK_i$ values were calculated based on a $K_D$ of 0.8 nM and a ligand concentration ([L]) of 0.8 nM according to the formula $K_i=(IC_{50})/(1+([L]/(KD)))$. Data are presented in Table 1.

TABLE 1

| Biological Data. | |
|---|---|
| EX | $K_i$ (nM) |
| 1 | 1 |
| 2 | 18 |
| 3 | 2 |
| 4 | 0.8 |
| 5 | 13 |
| 8 | 5 |
| 9 | 2 |
| 10 | 14 |
| 11 | 84 |
| 12 | 3 |
| 13 | 4 |
| 14 | 79 |
| 15 | 3 |
| 16 | 6 |
| 17 | 141 |
| 18 | 2 |
| 19 | 15 |
| 20 | 8 |
| 21 | 38 |
| 22 | 29 |
| 23 | 2 |
| 24 | 39 |
| 25 | 7 |
| 26 | 89 |
| 27 | 169 |
| 28 | 7 |

What is claimed is:
1. A compound selected from the group consisting of:
(4-Isopropyl-piperazin-1-yl)-(6-piperidin-1-ylmethyl-pyridin-3-yl)-methanone;
(4-Isopropyl-piperazin-1-yl)-(6-morpholin-4-ylmethyl-pyridin-3-yl)-methanone;
(4-Isopropyl-piperazin-1-yl)-(5-piperidin-1-ylmethyl-pyridin-2-yl)-methanone;
2-Piperdin-1-ylmethyl-5-(3-piperdin-1-yl-propoxy)-pyridine;
4-[5-(3-Piperidin-1-yl-propoxy)-pyridin-2-ylmethyl]-morpholine;
5-Piperidin-1-ylmethyl-2-(3-piperidin-1-yl-propoxy)-pyridine;
4-[6-(3-Piperidin-1-yl-propoxy)-pyridin-3-ylmethyl]-morpholine;
2-(4-Piperidin-1-yl-but-1-ynyl)-5-piperidin-1-ylmethyl-pyridine;
(4-Isopropyl-piperazin-1-yl)-[6-(2-piperidin-1-yl-ethylamino)-pyridin-3-yl]-methanone;
(4-Isopropyl-piperazin-1-yl)-[6-(2-morpholin-4-yl-ethylamino)-pyridin-3-yl]-methanone;
(4-Isopropyl-piperazin-1-yl)-[6-(2-pyridin-2-yl-ethylamino)-pyridin-3-yl]-methanone;
{6-[(2-Diethylamino-ethyl)-methyl-amino]-pyridin-3-yl}-(4-isopropyl-piperazin-1-yl)-methanone;
(4-Isopropyl-piperazin-1-yl)-[6-(4-isopropyl-piperazin-1-yl)-pyridin-3-yl]-methanone;
4-[5-(4-Isopropyl-piperazine-1-carbonyl)-pyridin-2-yl]-piperazine-1-carboxylic acid ethyl ester;
(4-Isopropyl-piperazin-1-yl)-[6-(4-methyl-piperazin-1-yl)-pyridin-3-yl]-methanone;
(4-Isopropyl-piperazin-1-yl)-[2-(2-piperidin-1-yl-ethylamino)-pyridin-4-yl]-methanone;
(4-Isopropyl-piperazin-1-yl)-[2-(2-piperidin-1-yl-ethylamino)-pyridin-3-yl]-methanone;
3-(4-Piperidin-1-yl-but-1-ynyl)-5-piperidin-1-ylmethyl-pyridine;

4-[5-(4-Piperidin-1-yl-but-1-ynyl)-pyridin-3-ylmethyl]-morpholine;
2-(4-Piperidin-1-yl-but-1-ynyl)-6-piperidin-1-ylmethyl-pyridine;
4-[6-(4-Piperidin-1-yl-but-1-ynyl)-pyridin-2-ylmethyl]-morpholine;
(2-Methoxy-ethyl)-[6-(4-piperidin-1-yl-but-1-ynyl)-pyridin-2-ylmethyl]-amine;
(4-Isopropyl-piperazin-1-yl)-(6-piperidin-1-ylmethyl-pyridin-3-yl)-methanethione, and enantiomers, diasteriomers and pharmaceutically acceptable salts and amides thereof.

2. A compound of claim 1 selected from the group consisting of:
(4-Isopropyl-piperazin-1-yl)-(6-piperidin-1-ylmethyl-pyridin-3-yl)-methanone;
(4-Isopropyl-piperazin-1-yl)-(6-morpholin-4-ylmethyl-pyridin-3-yl)-methanone;
(4-Isopropyl-piperazin-1-yl)-(5-piperidin-1-ylmethyl-pyridin-2-yl)-methanone;
2-Piperdin-1-ylmethyl-5-(3-piperdin-1-yl-propoxy)-pyridine;
4-[5-(3-Piperidin-1-yl-propoxy)-pyridin-2-ylmethyl]-morpholine;
2-(4-Piperidin-1-yl-but-1-ynyl)-5-piperidin-1-ylmethyl-pyridine;
(4-Isopropyl-piperazin-1-yl)-[6-(2-piperidin-1-yl-ethylamino)-pyridin-3-yl]-methanone;
(4-Isopropyl-piperazin-1-yl)-[6-(2-morpholin-4-yl-ethylamino)-pyridin-3-yl1-methanone;
{6-[(2-Diethylamino-ethyl)-methyl-amino]-pyridin-3-yl}-(4-isopropyl-piperazin-]-yl)-methanone;
(4-Isopropyl-piperazin-1-yl)-[6-(4-isopropyl-piperazin-1-yl)-pyridin-3-yl]-methanone;
(4-Isopropyl-piperazin-1-yl)-[6-(4-methyl-piperazin-1-yl)-pyridin-3-yl]-methanone;
(4-Isopropyl-piperazin-1-yl)-[2-(2-piperidin-1-yl-ethylamino)-pyridin-4-yl]-methanone;
3-(4-Piperidin-1-yl-but-1-ynyl)-5-piperidin-1-ylmethyl-pyridine;
4-[5-(4-Piperidin-1-yl-but-1-ynyl)-pyridin-3-ylmethyl]-morpholine;
2-(4-Piperidin-1-yl-but-1-ynyl)-6-piperidin-1-ylmethyl-pyridine;
4-[6-(4-Piperidin-1-yl-but-1-ynyl)-pyridin-2-ylmethyl]-morpholine;
(2-Methoxy-ethyl)-[6-(4-piperidin-1-yl-but-1-ynyl)-pyridin-2-ylmethyl]-amine;
(4-Isopropyl-piperazin-1-yl)-(6-piperidin-1-ylmethyl-pyridin-3-yl)-methanethione.

3. A compound of claim 2 selected from the group consisting of:
(4-Isopropyl-piperazin-1-yl)-(6-piperidin-1-ylmethyl-pyridin-3-yl)-methanone;
(4-Isopropyl-piperazin-1-yl)-(5-piperidin-1-ylmethyl-pyridin-2-yl)-methanone;
2-Piperdin-1-ylmethyl-5-(3-piperdin-1-yl-propoxy)-pyridine;
2-(4-Piperidin-1-yl-but-1-ynyl)-5-piperidin-1-ylmethyl-pyridine;
(4-Isopropyl-piperazin-1-yl)-[6-(2-piperidin-1-yl-ethylamino)-pyridin-3-yl]-methanone;
{6-[(2-Diethylamino-ethyl)-methyl-amino]-pyridin-3-yl}-(4-isopropyl-piperazin-1-yl)-methanone;
(4-Isopropyl-piperazin-1-yl)-[6-(4-isopropyl-piperazin-1-yl)-pyridin-3-yl]-methanone;
(4-Isopropyl-piperazin-1-yl)-[6-(4-methyl-piperazin-1-yl)-pyridin-3-yl]-methanone;
(4-Isopropyl-piperazin-1-yl)-[2-(2-piperidin-1-yl-ethylamino)-pyridin-4-yl]-methanone;
3-(4-Piperidin-1-yl-but-1-ynyl)-5-piperidin-1-ylmethyl-pyridine;
2-(4-Piperidin-1-yl-but-1-ynyl)-6-piperidin-1-ylmethyl-pyridine;
(4-Isopropyl-piperazin-1-yl)-(6-piperidin-1-ylmethyl-pyridin-3-yl)-methanethione.

4. A compound of claim 1 wherein said pharmaceutically acceptable salt is an effective amino addition salt.

5. A compound of claim 1 wherein said pharmaceutically acceptable salt is selected from the group consisting of hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate.

6. A pharmaceutical composition comprising a pharmaceutically acceptable carrier and a therapeutically effective amount of compound of claim 1 and enantiomers, diastereomers and pharmaceutically acceptable salts and amides thereof.

* * * * *